(12) United States Patent
Groneberg et al.

(10) Patent No.: US 8,039,639 B2
(45) Date of Patent: Oct. 18, 2011

(54) KINASE INHIBITORS AND METHODS OF USE THEREOF

(75) Inventors: Robert Groneberg, Boulder, CO (US); Laurence E. Burges, Boulder, CO (US); Darren Harvey, Boulder, CO (US); Ellen Laird, Boulder, CO (US); Mark C. Munson, Boulder, CO (US); James P. Rizzi, Boulder, CO (US); Martha Rodriguez, Boulder, CO (US); Charles Todd Eary, Boulder, CO (US); Daniel John Watson, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 13/020,578

(22) Filed: Feb. 3, 2011

(65) Prior Publication Data

US 2011/0124878 A1 May 26, 2011

Related U.S. Application Data

(62) Division of application No. 12/161,412, filed as application No. PCT/US2007/02272 on Jan. 26, 2007.

(60) Provisional application No. 60/763,712, filed on Jan. 31, 2006.

(51) Int. Cl.
 *C07D 231/56* (2006.01)
(52) U.S. Cl. .................................................. 548/362.5
(58) Field of Classification Search ................. 548/362.5
 See application file for complete search history.

(56) References Cited

U.S. PATENT DOCUMENTS

| | | | |
|---|---|---|---|
| 3,755,332 A | 8/1973 | Wasley et al. |
| 4,571,255 A | 2/1986 | Nielsen |
| 4,997,844 A | 3/1991 | Bernstein et al. |
| 5,234,942 A | 8/1993 | Bernstein et al. |
| 5,587,392 A | 12/1996 | Murakami et al. |
| 5,616,537 A | 4/1997 | Yokota et al. |
| 5,932,570 A | 8/1999 | Rodgers et al. |
| 5,945,418 A | 8/1999 | Bemis et al. |
| 6,080,763 A | 6/2000 | Regan et al. |
| 6,083,949 A | 7/2000 | Liverton et al. |
| 6,093,742 A | 7/2000 | Salituro et al. |
| 6,194,439 B1 | 2/2001 | Dow |
| 6,214,830 B1 | 4/2001 | Beers et al. |
| 6,228,881 B1 | 5/2001 | Regan et al. |
| 6,242,453 B1 | 6/2001 | Cirillo et al. |
| 6,297,239 B1 | 10/2001 | deSolms et al. |
| 6,297,381 B1 | 10/2001 | Cirillo et al. |
| 6,319,921 B1 | 11/2001 | Cirillo et al. |
| 6,355,636 B1 | 3/2002 | Wissner et al. |
| 6,358,945 B1 | 3/2002 | Breitfelder et al. |
| 6,432,995 B2 | 8/2002 | Hickey |
| 6,479,507 B2 | 11/2002 | Cheng et al. |
| 6,503,930 B1 | 1/2003 | Hanson et al. |
| 6,509,357 B1 | 1/2003 | Zhou et al. |

(Continued)

FOREIGN PATENT DOCUMENTS

CN 1235602 A 11/1999

(Continued)

OTHER PUBLICATIONS

Aleshin, Alexey et al., "Myocardial Protective Effect of FR167653: A Novel Cytokine Inhibitor in Ischemic-Reperfused Rat Heart", European Journal of Cardio-Thoracic Surgery. 26(5), 974-980, (2004).
Badger, Alison M. et al., "Disease-Modifying Activity of SB 242235, a Selective Inhibitor of p38 Mitogen-Activated Protein Kinase, in Rat Adjuvant-Induced Arthritis", Arthritis & Rheumatism, 43(1), 175-183, (2000).

(Continued)

*Primary Examiner* — Rebecca Anderson
(74) *Attorney, Agent, or Firm* — John R. Moore, Esq.; Sarah S. Mastous

(57) ABSTRACT

A compound of Formula II

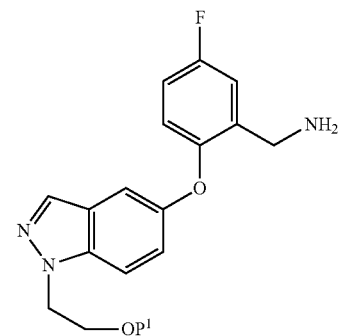

and salts thereof are useful in the preparation of a compound of Formula I

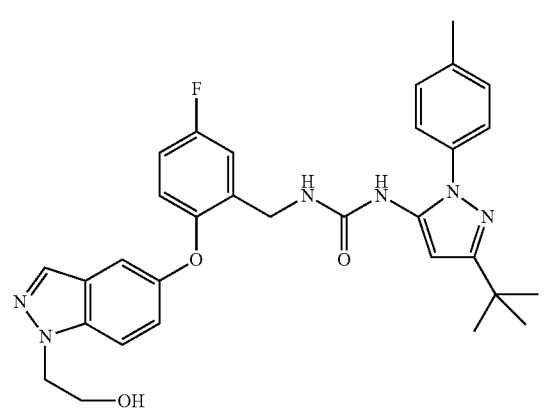

and pharmaceutically acceptable salts and prodrugs thereof.

1 Claim, No Drawings

U.S. PATENT DOCUMENTS

| | | | |
|---|---|---|---|
| 6,531,491 | B1 | 3/2003 | Kania et al. |
| 6,589,954 | B1 | 7/2003 | Mavunkel et al. |
| 6,608,058 | B2 | 8/2003 | Yoon et al. |
| 6,696,464 | B2 | 2/2004 | McClure et al. |
| 6,716,978 | B2 | 4/2004 | Marfat |
| 6,743,795 | B1 | 6/2004 | Yoon et al. |
| 6,821,966 | B2 | 11/2004 | Dugar et al. |
| 6,825,184 | B2 | 11/2004 | Cirillo et al. |
| 6,858,638 | B2 | 2/2005 | Damour et al. |
| 6,894,173 | B2 | 5/2005 | Zhang et al. |
| 6,949,579 | B2 | 9/2005 | Dutruc-Rosset et al. |
| 7,041,669 | B2 | 5/2006 | Cirillo et al. |
| 7,102,009 | B2 | 9/2006 | Patel et al. |
| 7,105,682 | B2 | 9/2006 | Chen et al. |
| 7,129,252 | B2 | 10/2006 | Chen |
| 7,135,575 | B2 | 11/2006 | Munson et al. |
| 7,166,629 | B2 | 1/2007 | Lesuisse et al. |
| 7,196,082 | B2 | 3/2007 | Doherty et al. |
| 7,199,147 | B2 | 4/2007 | Imazaki et al. |
| 7,414,132 | B2 | 8/2008 | De La Torre et al. |
| 7,511,136 | B2 | 3/2009 | Amici et al. |
| 7,521,447 | B2 | 4/2009 | Munson et al. |
| 7,589,112 | B2 | 9/2009 | Buchstaller et al. |
| 7,655,802 | B2 | 2/2010 | Schumacher et al. |
| 7,737,153 | B2 | 6/2010 | Feurer et al. |
| 7,799,782 | B2 | 9/2010 | Munson et al. |
| 2003/0220241 | A1 | 11/2003 | Defeo-Jones et al. |
| 2004/0180896 | A1 | 9/2004 | Munson et al. |
| 2004/0192654 | A1 | 9/2004 | Gourdeau et al. |
| 2006/0241127 | A1 | 10/2006 | Feurer et al. |
| 2006/0264431 | A1 | 11/2006 | Munson et al. |
| 2009/0023795 | A1 | 1/2009 | Groneberg et al. |
| 2009/0048301 | A1 | 2/2009 | Chen et al. |
| 2009/0143422 | A1 | 6/2009 | Munson et al. |
| 2009/0149459 | A1 | 6/2009 | Munson et al. |

FOREIGN PATENT DOCUMENTS

| | | | |
|---|---|---|---|
| EA | 20000385 | A1 | 10/2000 |
| EA | 200000488 | A1 | 10/2000 |
| EA | 002113 | B1 | 12/2001 |
| EP | 0293978 | | 12/1988 |
| EP | 0448206 | | 9/1991 |
| EP | 0684235 | | 11/1995 |
| EP | 1403255 | A1 | 3/2004 |
| JP | 59098060 | | 6/1984 |
| JP | 63068568 | | 3/1988 |
| RU | 2004129780 | A | 4/2005 |
| RU | 2004130280 | A | 6/2005 |
| RU | 2005104820 | A | 10/2005 |
| RU | 2005109561 | A | 11/2005 |
| SU | 1545940 | A3 | 2/1990 |
| SU | 1595338 | A3 | 9/1990 |
| WO | 92/21660 | | 12/1992 |
| WO | 97/12876 | A1 | 4/1997 |
| WO | 98/09961 | A1 | 3/1998 |
| WO | 98/13350 | A1 | 4/1998 |
| WO | 98/20008 | A1 | 5/1998 |
| WO | 98/43960 | A1 | 10/1998 |
| WO | 99/17777 | A1 | 4/1999 |
| WO | 99/23076 | A1 | 5/1999 |
| WO | 99/23077 | A1 | 5/1999 |
| WO | 00/17170 | A2 | 3/2000 |
| WO | 00/43384 | A1 | 7/2000 |
| WO | 00/59930 | A1 | 10/2000 |
| WO | 00/66583 | A1 | 11/2000 |
| WO | 00/71535 | A1 | 11/2000 |
| WO | 01/02369 | A2 | 1/2001 |
| WO | 01/38306 | A1 | 5/2001 |
| WO | 01/78648 | A2 | 10/2001 |
| WO | 02/42292 | A2 | 5/2002 |
| WO | 02/059088 | A1 | 8/2002 |
| WO | 02/068406 | A2 | 9/2002 |
| WO | 02/072579 | A1 | 9/2002 |
| WO | 02/100833 | A1 | 12/2002 |
| WO | 03/028720 | A1 | 4/2003 |
| WO | 03/032989 | A1 | 4/2003 |
| WO | 03/051847 | A1 | 6/2003 |
| WO | 03/072569 | A1 | 9/2003 |
| WO | 03/087072 | A1 | 10/2003 |
| WO | 2004/007481 | A2 | 1/2004 |
| WO | 2004/009557 | A1 | 1/2004 |
| WO | 2004/037789 | A2 | 5/2004 |
| WO | 2004/039796 | A2 | 5/2004 |
| WO | 2004/052280 | A2 | 6/2004 |
| WO | 2004/078116 | A2 | 9/2004 |
| WO | 2004/100946 | A1 | 11/2004 |
| WO | 2004/113303 | A1 | 12/2004 |
| WO | 2005/000232 | A2 | 1/2005 |
| WO | 2005/004818 | A2 | 1/2005 |
| WO | 2005/023761 | A2 | 3/2005 |
| WO | 2005/063715 | A1 | 7/2005 |
| WO | 2005/066164 | A1 | 7/2005 |
| WO | 2007/089646 | A1 | 8/2007 |

OTHER PUBLICATIONS

Birkenkamp, K.U. et al., "Differential Effects of Interieukin-3 and Interleukin-I on the Proliferation and Interleukin-6 Protein Secretion of Acute Myeloid Leukemic Cells; The involvement of ERK, p38 and STAT5", European Cytokine Network, 10(4), 479-490, (1999).

Branger, Judith et al., "Inhibition of Coagulation, Fibrinolysis and Endothelial Cell Activation by a p38 Mitogen-Activated Protein Kinase Inhibitor During Human Endotoxemia", Blood, 101(11), 4446-4448, (2003).

Brown, Kimberly K. et al., "P38 MAP Kinase Inhibitors as Potential Therapeutics for the Treatment of Joint Degeneration and Pain Associated with Osteoarthritis", Journal of Inflammation, 5(22), 8 pages, (2008).

Cau, Jerome, et al., "FR167653 Improves Renal Recovery and Decreases Inflammation and Fibrosis After Renal Ischemia Reperfusion Injury", Journal for Vascular Surgery, 49(3), 728-740, (2009).

Chen, Xu-Lin et al., "Role of p38 Mitogen-Activated Protein Kinase in Lung Injury after Burn Trauma", Shock, 19(5), 475-479, (2003).

Clark, James E. et al., "Potential of p38-MAPK Inhibitors in the Treatment of Ischaemic Heart Disease", Pharmacology and Therapeutics, 116, 192-206, (2007).

Cottrell, Jessica A. et al., "Analgesic Effects of p38 Kinase Inhibitor Treatment on Bone Fracture Healing", Pain, 142(1-2), 116-126, (2009).

Denkert, Carsten et al., "An Inhibitor of Stress-Activated MAP-Kinases Reduces Invasion and MMP-2 Expression of Malignant Melanoma Cells", Clinical and Experimental Metastasis, 19, 79-85, (2002).

Doucet, Carole et al., "A p38 Mitogen-Activated Protein Kinase Inhibitor Protects Against Renal Damage in a Non-Heart-Beating Donor Model", American Journal of Physiology—Renal Physiology, 295(1), FI79-191, (2008).

Duan, Wei et al., "Inhaled p38a Mitogen-Activated Protein Kinase Antisense Oligonucleotide Attenuates Asthma in Mice", Am. 1. Respir. Crit. Care Med., 171, 571-578, (2005).

Fijen, J.W. et al., "Suppression of the Clinical Cytokine Response to Endotoxin by RWJ-67657, a p38 Mitogen-Activated Protein-Kinase Inhibitor, in Healthy Human Volunteers", Clin. Exp. Immunol., 124(1),16-20, (2001).

Giafis, Nick et al., "Role of the p38 Mitogen-Activated Protein Kinase Pathway in the Generation of Arsenic Trioxide-Dependent Cellular Responses", Cancer Research, 66(13), 6763-6771, (2006).

Hideshima, Teru et al., "Targeting p38 MAPK Inhibits Multiple Myeloma Cell Growth in the Bone Marrow Milieu", Blood, 101(2), 703-705, (2003).

Hoesel, Laszlo M. et al., "Local Wound p38 MAPK Inhibition Attenuates Burn-Induced Cardiac Dysfunction," Surgery, 146(4), 775-785, (2009.

Hollenbach, Eike et al., "Inhibition of p38 Map Kinase- and RICK/NF-kB-Signaling Suppresses Inflammatory Bowel Disease", FASEB Journal, 18(13), 1550-1552, (2004).

Ipaktchi, Kyros et al., "Attenuating Burn Wound Inflammatory Signaling Reduces Systemic Inflammation and Acute Lung Injury", Journal of Immunology, 177(11), 8065-8071, (2006).

Jackson, Jeffery R. et al., "Pharmacological Effects of SB 220025, a Selective Inhibitor of p38 Mitogen-Activated Protein Kinase, in Angiogenesis and Chronic Inflammatory Disease Models", Journal of Pharmacology and Experimental Therapeutics, 284(2), 687-692, (1998).

Kent, Lauren M. et al., "Inhibition of Lipopolysaccharide-Stimulated Chronic Obstructive Pulmonary Disease Macrophage Inflammatory Gene Expression by Dexamethasone and the p38 Mitogen-Activated Protein Kinase Inhibitor N-cyano-N'-(2-{[8-(2,6-difluorophenyl)-4-(4-fluoro-2-methylphenyl)-7-oxo-7,8-dihydropyrido[2,3-d]pyrimidin-2-yl]amino}ethyl)guanidine (SB706504)", Journal of Pharmacology and Experimental Therapeutics, 328(2), 458-468, (2008).

Koshikawa, Masao et al., "Role of p38 Mitogen-Activated Protein Kinase Activation of Podocyte Injury and Proteinuria in Experimental Nephrotic Syndrome", J. Am. Soc. Nephrol., 16(9),2690-2701, (2005).

Li, Zhihe et al., "Selective Inhibition of p38a MAPK Improves Cardiac Function and Reduces Myocardial Apoptosis in Rat Model of Myocardial Injury", American Journal of Physiology, Heart Circular Physiology, 291(4), H1972-1977, (2006).

Liu, Ru et al., "Extracellular Signal-Regulated Kinase 1/Extracellular Signal-Regulated Kinase 2 Mitogen-Activated Protein Kinase Signaling and Activation of Activator Protein 1 and Nuclear Factor kB Transcription of Factors Play Central Roles in Interleukin-8 Expression Stimulated by Monosodium Urate Monohydrate and Calcium Pyrophosphate Crystals in Monocytic Cells", Arthritis & Rheumatism. 43(5), 1145-1155, (2000).

Maulik, Nilanjana, "Effect of p38 MAP Kinase on Cellular Events During Ischemia and Reperfusion:. Possible Therapy", American Journal of Physiology, Heart Circular Physiology, 289, H2302-2303, (2005).

Mbalaviele, Gabriel et al., "Inhibition of p38 Mitogen-Activated Protein Kinase Prevents. Inflammatory Bone Destruction", Journal of Pharmacology and Experimental Therapeutics, 317(3), 1044-1053, (2006).

Medicherla, Satyanarayana et al., "p38a-Selective MAP Kinase Inhibitor Reduces Tumor Growth in Mouse Xenograft Models of Multiple Myeloma", Anticancer Research, 28, 3827-3834, (2008).

Medicherla, Satyanarayana et al., "p38a-Selective Mitogen-Activated Protein Kinase Inhibitor SD-282 Reduces Inflammation in a Subchronic Model of Tobacco Smoke-Induced Airway Inflammation", Journal of Pharmacology and Experimental Therapeutics, 324(3), 921-929, (2008).

Medicherla, Satyanarayana et al., "Preventive and Therapeutic Potential of p38 alpha-Selective Mitogen-Activated Protein Kinase Inhibitor in Nonobese Diabetic Mice with Type 1 Diabetes", Journal of Pharmacology and Experimental Therapeutics, 318(1), 99-107, (2006).

Mihara, K. et al., "A Potent and Selective p38 Inhibitor Protects Against Bone Damage in Murine Collagen-Induced Arthritis: A Comparison with Neutralization of Mouse, TNFa", British Journal of Pharmacology, 154, 153-164, (2008).

Nath, Puneeta et al., "Importance of p38 Mitogen-Activated Protein Kinase Pathway in Allergic. Airway Remodelling and Bronchial Hyperresponsiveness", European Journal of Pharmacology, 544, 160-167, (2006).

Nishikori, Tomohiro et al., "Anti-Inflammatory Potency of FR167653 a p38 Mitogen-Activated Protein Kinase Inhibitor, in Mouse Models of Acute Inflammation", European Journal of Pharmacology, 451,327-333, (2002).

Nguyen, Aaron N. et al., "Normalizing the Bone Marrow Microenvironment with p38 Inhibitor Reduces Multiple Myeloma Cell Proliferation and Adhesion and Suppresses Osteoclast Formation", Experimental Cell Research, 312, 1909-1923, (2006).

Pelletier, Jean-Pierre et al., "Chondrocyte Death in Experimental Osteoarthrities is Mediated by MEK 112 and p38 Pathways: Role of Cyclooxygenase-2 and Inducible Nitric Oxide Synthase", Journal of Rheumatology, 28(11), 2509-2519, (2001).

Peng, Tianqing et al., "Inhibition of p38 MAPK Decreases Myocardial TNF-alpha Expression and Improves Myocardial Function and Survival in Endotoxemia", Cardiovascular Research, 59, 893-900, (2003).

Piao, Chun Shu et al., "Administration of the p38 MAPK Inhibitor SB203580 Affords Brain Protection with a Wide Therapeutic Window Against Focal Ischemic Insult", Journal of Neuroscience Research. 73(4), 537-544, (2003).

Pouliot, Marc et ai., "Monosodium Urate Microcrystals Induce Cyclooxygenase-2 in Human Monocytes", Blood, The American Society of Hematology, 91(5), 1769-1776, (1998).

Riad, Alexander et al., "Chronic Inhibition of p38MAPK Improves Cardiac and Endothelial Function in Experimental Diabetes Mellitus", European Journal of Pharmacology, 554(1),40-45, (2007).

Remmers, Ann E. et al., "Potent Clinical Anti-Inflammatory and Analgesic Activity of a Novel p38a Inhibitor ARRY797", Arthritis Rheum., 58, S298-S299, (2008).

Sang, Isao et al., "Prolonged Survival of Rat Cardiac Allograft with Proinflammatory Cytokine Inhibitor", Journal of Heart and Lung Transplantation, 20(5), 583-589, (2001).

Sheryanna, Abdulmunem et al., "Inhibition of p38 Mitogen-Activated Protein Kinase is Effective in the Treatment of Experimental Crescentic Glomerulonephritis and Suppresses Monocyte Chemoattractant Protein-I but Not IL-IB or IL-6", J. Am. Soc. Nephrol., 18(4), 1167-1179, (2007).

Sodhi, Akrit et al., "The Kaposi's Sarcoma-Associated Herpes Virus G Protein-Coupled Receptor Up-Regulates Vascular Endothelial Growth Factor Expression and Secretion Through Mitogen-Activated Protein Kinase and p38 Pathways Acting on Hypoxia-Inducible Factor 1a", Cancer Research, 60, 4873-4880, (2000).

Stambe, Cosimo et al., "Blockade of p38a MAPK Ameliorates Acute Inflammatory Renal Injury in Rat Anti-GBM Glomerulonephritis", Journal of the American Society of Nephrology, 14, 338-351, (2003).

Tong, S.E. et al., "SCIO-469: A Novel p38a MAPK Inhibitor, Provides Efficacy in Acute Post-Surgical Dental Pain", Clinical Pharmacology & Therapeutics, 75(2), 3, (2004).

Wang, Yi Xin et al., "Activation and Clinical Significance of p38 MAPK Signaling Pathway in Patients with Severe Trauma", Journal of Surgical Research, 1-7, (2009).

Wen, Jianguo et al., "P38 MAPK Inhibition Enhancing a TO-Induced Cytotoxicity Against Multiple Myeloma Cells", British Journal of Haematology, 140, 169-180, (2008).

Wood, Lisa et al., "The Cancer Chemotherapy Drug Etoposide (VP-16) Induces Pro inflammatory Cytokine Production and Sickness Behavior-like Symptoms in a Mouse Model of Cancer Chemotherapy-Related Symptoms", Biological Research for Nursing, 8(2),157-169, (2006).

Zhao, Fang et al., "Activation of p38 Mitogen-Activated Protein Kinase Drives Dendritic Cells to Become Tolerogenic in Ret Transgenic Mice Spontaneously Developing Melanoma", Clinical Cancer Research, 15(13), 4382-4390, (2009).

Boehm, J.C. and J. L. Adams, "New inhibitors of p38 kinase", Expert Opinion on Therapeutic Patents, 10, 25-37, (2000).

Branger, Judith et al., "Anti-Inflammatory Effects of a p38 Mitogen-Activated Protein Kinase Inhibitor During Human Endotoxemia," Journal of Immunology ,168, 4070-4077, (2002).

Damasio, A. R., "Alzheimers Disease and Related Dementias," Cecil Textbook of Medicine, 20th edition, 2, 1992-1996, (1996).

FDA mulls drug to slow late-stage Alzheimer's [online], [retrieved on Sep. 23, 2003]. Retrieved from the Internet, URL: http://www .cnn. com/20031HEAL TH/conditions/09/24/alzheimers.drug.ap/index. html>.

Foster, M. L. et al., "Potential p38 Inhibitors in the Treatment of Rheumatoid Arthritis", Drug News Perspect., 13(8), 488-497, (Oct. 2000).

Golub, T. R. et al., "Molecular Classification of Cancer: Class Discovery and Class Prediction by Gene Expression Monitoring", Science, 286, 531-537, (1999).

Huff, Joel R., "HIV protease: a novel chemotherapeutic target for AIDS", Journal of Medicinal Chemistry, 34(8), 2305-2314, (Aug. 1991).

Lala, P. K. and A. Orucevic, "Role of nitric oxide in tumor progression: Lessons from experimental tumors", Cancer and Metastasis Reviews, 17(1), 91-106, (1998).

Layzer, R. B., "Section Five—Degenerative Diseases of the Nervous System", Cecil Textbook of Medicine, 20th edition, vol. 2, 2050-2057, (1996).

Mandel, Silvia et al., "Neuroprotective Strategies in Parkinson's Disease: An Update on Progress" CNS Drugs, 17(10), 729-62, (2003).

Natarajan, Swaminathan R. et al., "P38 MAP Kinase inhibitors. Part 1: Design and Development of a New Class of Potent and Highly Selective Inhibitors Based on 3,4-Dihydropyrido, (3,2-d 1 Pyrimidone Scaffold", Biorganic and Medicinal Chemistry Letters, 13, 273-276, (2003).

Owens, R. J. et ai, "Therapeutic Regulation of Cytokine Signaling by Inhibitors of p38 Mitogen-Activated Protein Kinase," Novel Cytokine Inhibitors, Eds. Gerry A. Higgs and Brian Henderson, 201-211, (2000).

Salituro, E. G. et al. "Inhibitors of p38 MAP Kinase: Therapeutic Intervention in Cytokine-Mediated Diseases", Current Medicinal Chemistry, 6(9), 807-823, (1999).

Boyer, Gerard et al., "Synthesis of Pyrazolo[a]acridin-9(10H)ones", Journal of Chemical Research Synopses, 11,350-1, (1990), Database Caplus [online], Chemical Abstracts Service, 2 pgs., 1991: 10 1818, XP-002399804.

Database Caplus [online], "Indazoles", Chemical Abstracts Service, 2 pgs. 1984:571244, XP002399803, including JP 59-098060 (Fujisawa Pharmaceutical Co., Ltd., Japan), Jun. 6, 1984.

Database CAS Online on STN, Chern. Abstr. Accession No. 2002:964330, "Preparation of heterocyclic compounds as Rho-kinase inhibitors", WO 2002100844 AL (Sumitomo Pharmaceuticals Company, Limited, Japan) Dec. 19, 2002, abstract.

Database WPI, "New Para-aminophenol derivatives," Derwent Publications Ltd., 2 pgs., 1988-123677, XP002399810, including JP 63-068568 (Otsuka), compound 7, p. 538, Mar. 28, 1988.

Haas, Georges et al., "The Synthesis of Pyridine Derivatives from 3-Formylchromone", Journal of Heterocyclic Chemistry, 18(3), 607-612, (1981), XP002399802, compound 17.

Kamel, M. et al., "Studios on Some New Indazole and Benzimidazole Derivatives", Journal Fuer Praktische Chemie (Leipzig), 31(1-2), 100-108, (1966), XP002399801, compounds VI, VIII.

Kovendi, Alexander et al., "Isonitrosation. I. Isonitrosation of Substituted Ethylnitrobenzenes" Chemische Berichte, 97(7), 1902-9, (1964), XP002427247.

Lee, Hee Jae et al., "Biochemical and Physiological Effects of Benzheterocycles and Related Compounds", Journal of Agriculture and Food Chemistry, 43(10), 2722-7, (1995), XP000612804.

Mefetah, Hafid et al., "Potential Anticancer Benzo-Napthyridones with Fused Rings: a theor. model for predicting orientation in the cyclization of intermediates," Medicinal Chemistry Research, 5(7), 522-33, (1995), Database Caplus [online], Chemical Abstracts Service, 1 pg., 1995:918180, XP-002399805.

Morel, Sandrine et al., "A Synthesis of 9-Methoxy-1-Methyl-1H, 6H-Pyrazolo(4,3-c) Carbazole" Synthetic Communications, 26(13), 2443-2447, (1996), Database Caplus, Chemical Abstracts Service, STN Database Accession No. 1996:355466, XP002427248.

Nagarajan, K. et al., "Quest for Anthelmintic Agents. Part II. Benzothiazole and Benzotriazole Carbamates and 2-Benzazolyl Vinyl Ketones", Indian Journal of Pharmaceutical Sciences, 48(4),85-8, 91, (1986), Database Caplus, Chemical Abstracts Service, STN Database Accession No. 1987: 148991, XP-002427251.

Patent Cooperation Treaty, International Search Report & Written Opinion of the International Search Authority, PCT/US2007/002272, May 31, 2007,8 pages.

Quiroga, Jairo et al., "Synthesis of Pyrazolo[3,4-b ]Pyridines and Pyrido[2,3-d]Pyrirnidinones by Hetero-Diels-Alder Reaction of Pyrazolyl- and Pyrimidinylimines Under Microwave Irradiation in Dry Media", Heterocyclic Communications, 6(4), 345-350, (2000), Database Caplus [online], Chemical Abstracts Service, 2 pgs., 2000:806043, XP-002399806.

Tarabasanu-Mihaila, C. et al.. "Heterocyclic Compact Condensed Systems. IV. Linear Bispyrazolo[2,3-d], [8,9-d]Trans-Quinacridone", Revue Roumaine De Chimie, 23(7), 1079-84, (1978), Database Caplus, Chemical Abstracts Service, STN Database Accession No. 1979:24765, XP-002427250.

Office Action issued by the Russian Federation Patent Office and translation thereof, dated May 10, 2007, 28 pages.

Zhang, Xiaowei (Patent Agent), Office Action issued by the Chinese Patent Office and Translation thereof, issued Jul. 20, 2007, 8 pages.

Vippagunta, S.R., et al., "Crystalline Solids", Advanced Drug Delivery Reviews, 48, 3-26 (2001).

Cancer [online], [retrieved on Jun. 7, 2007]. Retrieved from the Internet, URL; http://www.nlm.nih.gov/medlineplus/cancer.html>.

Cancer [online], [retrieved on Jun. 7, 2006]. Retrieved from the Internet, URL; http://en.wikipedia.org/wiki/Cancer>.

Badger, Alison M. et al., "Pharmacological Profile of SB 203580, a Selective Inhibitor of Cytokine Suppressive Binding Protein/p38 Kinase, in Animal Models of Arthritis, Bone Resorption, Endotoxin Shock and Immune Function," Journal of Pharmacology and Experimental Therapeutics, 279(3), 1453-1461, (1996).

KINASE INHIBITORS AND METHODS OF USE THEREOF

This application is a divisional of U.S. Ser. No. 12/161,412, filed Jul. 18, 2008, which is a Section 371(e) filing from PCT/US07/02272, filed Jan. 26, 2007, which claims the benefit of U.S. provisional patent application No. 60/763,712 filed on Jan. 31, 2006, each of which is incorporated herein in its entirety.

BACKGROUND OF THE INVENTION

1. Field of the Invention

This invention relates to kinase inhibitors, pharmaceutical compositions containing the inhibitors, and methods for preparing these inhibitors. The kinase inhibitors of this invention are useful for the treatment of inflammation, osteoarthritis, rheumatoid arthritis, cancer, autoimmune diseases, and other cytokine-mediated diseases.

2. Description of the State of the Art

A number of chronic and acute inflammatory conditions have been associated with the overproduction of pro-inflammatory cytokines. Such cytokines include but are not limited to tumor necrosis factor alpha (TNF-α), interleukin 1 beta (IL-1β), interleukin 8 (IL-8) and interleukin 6 (IL-6). Rheumatoid arthritis (RA) is a chronic disease where TNF-α and IL-1α are implicated in the onset of the diseases and in the progression of the bone and joint destruction seen with this debilitating condition. Recently approved therapeutic treatments for RA have included soluble TNF-α receptor (ENBREL™) and IL-1 receptor antagonist (ANAKINRA™). These treatments work by blocking the ability of their respective cytokines to bind to their natural receptors. Alternative methods for treating cytokine-mediated diseases are currently under investigation. One such method involves inhibition of the signaling pathway that regulates the synthesis and production of pro-inflammatory cytokines such as p38.

P38 (also known as CSBP or RK) is a serine/threonine mitogen-activated protein kinase (MAPK) that has been shown to regulate pro-inflammatory cytokines P38 MAPK was first identified as a kinase that becomes tyrosine phosphorylated in mouse monocytes following treatment with lipopolysaccharide (LPS). A link between p38 MAPK and the response of cells to cytokines was first established by Saklatvala et al., (*Cell*, 1994, 78:1039-1049), who showed that IL-1 activates a protein kinase cascade that results in the phosphorylation of the small heat shock protein, Hsp27, probably by mitogen-activated protein activated protein kinase 2 (MAPKAP kinase-2). Analysis of peptide sequences derived from the purified kinase indicated that it was related to the p38 MAPK activated by LPS in mouse monocytes (Han, J., et al., *Science*, 1994, 265:808-811). At the same time it was shown that p38 MAPK was itself activated by an upstream kinase in response to a variety of cellular stresses, including exposure to UV radiation and osmotic shock, and the identity of the kinase that directly phosphorylates Hsp27 was confirmed as MAPKAP kinase-2 (Rouse, J., et al., *Cell*, 1994, 78:1027-1037). Subsequently, it was shown that p38 MAPK was the molecular target of a series of pyridinylimidazole compounds that inhibited the production of TNF from LPS-challenged human monocytes (Lee, J., et al., *Nature*, 372:739-746). This was a key discovery and has led to the development of a number of selective inhibitors of p38 MAPK and the elucidation of its role in cytokine signaling.

It is now known that multiple forms of p38 MAPK (α, β, γ, δ), each encoded by a separate gene, form part of a kinase cascade involved in the response of cells to a variety of stimuli, including osmotic stress, UV light, and cytokine mediated events. These four isoforms of p38 are thought to regulate different aspects of intracellular signaling. Activation of p38 is part of a cascade of signaling events that lead to the synthesis and production of pro-inflammatory cytokines such as TNF-α. P38 functions by phosphorylating downstream substrates that include other kinases and transcription factors. Agents that inhibit p38 MAPK have been shown to block the production of cytokines including but not limited to TNF-α, IL-6, IL-8 and IL-1β in vitro and in vivo models (Adams, J. L., et al., *Progress in Medicinal Chemistry*, 2001, 38:1-60).

Abl (also known as Ableson) is a tyrosine kinase that is expressed in hematopoietic cells and is implicated in the progression of various liquid tumors including chronic myeloid leukemia (CML) and acute lymphoblastic leukemia (ALL). Transformation is a result of a chromosomal translocation, known as the Philadelphia chromosome. This leads to a constitutively activated chimera between Ableson and the breakpoint cluster region (BCR)—the Abl-BCR protein. GLEEVEC®, also known as Imatinib (Novartis) is a potent inhibitor of Abl and is currently used to treat CML patients (*N. Engl. J. Med.*, 2001, 344:1031-1037). This drug has become the standard of care for this deadly disease and is also being looked at in a variety of other cancer settings including gastrointestinal stromal tumors (GIST).

There is evidence that fibroblasts respond to the growth factor protein TGF-β by stimulating the Abl pathway and lead to morphological changes indicative of fibrosis; therefore Abl could play a role in the pathogenesis of fibrotic diseases like idiopathic pulmonary fibrosis. Leof et al. (*J. Clin. Invest.*, 2004, 114(9) 1308-1316) have demonstrated pre-clinical efficacy of GLEEVEC® in a bleomycin-mediated model of lung fibrosis in mice. GLEEVEC® is being evaluated in patients with pulmonary fibrosis.

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis (Maisonpierre et al., *Science*, 1997, 277:55-60). Tie2 is up-regulated in tumor angiogenic vessels (Trogan, E. *Br. J. Cancer*, 1998, 77:51-56) and there is evidence that it may play a supportive role in hematopoietic cancers (L. Naldini et al., *Cancer Cell*, 2005, 8:211-226; Suda, T. et al., *Cell*, 2004, 118:149-161). In addition to its possible role in cancer, angiogenesis may also have implications in diseases like rheumatoid arthritis (RA), psoriasis and the progression of inflammation driven pathologies. The formation of pannus, the destructive legion responsible for arthritic progression is in part driven by new blood vessel formation and a recent paper by Lin, C. et al. (*Arthritis and Rheumatism*, 2005, 52(5): 1585-1594) demonstrates the pathological role of Tie2 in a mouse collagen-induced arthritis models of RA. Therefore, inhibition of Tie2 could provide a beneficial effect against proliferative and inflammatory diseases.

Several other kinases have been implicated in the progression of proliferative diseases such as cancer. Among these, numerous Src family member proteins have been shown to play a similar role as Src and may provide parallel signaling pathways during uncontrolled cellular proliferation. Primary examples include the tyrosine kinases Lyn, Fyn, Lck and Hck.

Lyn and Hck have been implicated in the progression of B-cell acute lymphoblastic leukemia (B-ALL), a hematopoietic cancer of B cells (Li, S. et al. *Nat. Genet.*, 2004 36(5): 453-461).

The Eph (erythropoietin-producing hepatoma amplified sequence) family of tyrosine kinase receptors binds ephrins which leads to numerous cellular processes. Ephs appear to play a role modulating tumour cell adhesion and motility and invasiveness, and some evidence demonstrates an active role of Ephs and ephrins in neo-vascularisation during pathological processes. The Eph A receptors are over-expressed in lung, kidney and gastric tumour vasculature, and dominant-negative, soluble EphA2 or A3 proteins have been shown to modulate tumour angiogenesis and progression in vivo (Lackmann M. et al., *IUBMB Life*, 2005, 57(6):421-31).

Vascular endothelial growth factors and their cognate receptors, for example KDR (VEGFR2) and FLT1 (VEGFRR1) are key regulators of angiogenesis. The protein therapeutic drug AVASTIN® has shown promise in colon cancer and works through the VEGFR pathway. SUTENT/SU11248 (sunitinib malate) (Pfizer) is a potent KDR inhibitor and has shown promising results against GIST and renal cell carcinomas.

Peripheral blood monocytes (PBMCs) have been shown to express and secrete pro-inflammatory cytokines when stimulated with lipopolysaccharide (LPS) in vitro. P38 inhibitors efficiently block this effect when PBMCs are pretreated with such compounds prior to stimulation with LPS (Lee, J. C., et al., *Int. J. Immunopharmacol.*, 1988, 10:835-843). The efficacy of p38 inhibitors in animal models of inflammatory disease has prompted an investigation of the underlying mechanism(s) which could account for the effect of these inhibitors. The role of p38 in the response of cells to IL-1 and TNF has been investigated in a number of cells systems relevant to the inflammatory response using a pyridinyl imidazole inhibitor: endothelial cells and IL-8 (Hashimoto, S., et al., *J. Pharmacol. Exp. Ther.*, 2001, 293:370-375), fibroblasts and IL-6/GM-CSF/PGE2 (Beyaert, R., et al., *EMBO J.*, 1996, 15:1914-1923), neutrophils and IL-8 (Albanyan, E. A., et al., *Infect. Immun.*, 2000, 68:2053-2060) macrophages and IL-1 (Caivano, M. and Cohen, P., *J. Immunol.*, 2000, 164:3018-3025), and smooth muscle cells and RANTES (Maruoka, S., et al., *Am. J. Respir. Crit. Care Med.*, 1999, 161:659-668). The destructive effects of many disease states are caused by the over production of pro-inflammatory cytokines. The ability of p38 inhibitors to regulate this overproduction makes them excellent candidates for disease modifying agents.

Known inhibitors of p38 MAPK are active in a variety of widely recognized disease models. Inhibitors of p38 MAPK show positive effects in a number of standard animal models of inflammation including rat collagen-induced arthritis (Jackson, J. R., et al., *J. Pharmacol. Exp. Ther.*, 1998, 284: 687-692); rat adjuvant-induced arthritis (Badger, A. M., et al., *Arthritis Rheum.*, 2000, 43:175-183; Badger, A. M., et al., *J. Pharmacol. Exp. Ther.*, (1996) 279:1453-1461); and carrageenan-induced paw edema in the mouse (Nishikori, T., et al., *Eur. J. Pharm.*, 2002, 451:327-333). Molecules that block the function of p38 have been shown to be effective in inhibiting bone resorption, inflammation, and other immune and inflammation-based pathologies in these animal models.

Thus, a safe and effective kinase inhibitor would provide a means to treat debilitating diseases that can be regulated by modulation of one or more kinases.

International patent application publication number WO 2004/078116 discloses certain compounds as kinase inhibitors. Amongst these compounds are certain N1-substituted indazole derivatives having a substituent at the 5-position that contains a pyrazol-5-ylurea group. Examples of such compounds include the compounds of Examples 94 and 138 in which the N1 substituent is respectively a methyl group and a 2-hydroxy-2-methylpropyl group.

It has now been found that compounds having particularly desirable properties may be obtained by selecting the primary alcohol group, —CH$_2$CH$_2$OH, as the N1 substituent, and a particular substituent at the 5-position containing a 3-tert-butyl-1-p-tolyl-1H-pyrazol-5-yl group.

SUMMARY OF THE INVENTION

This invention provides compounds that inhibit one or more kinases and kinase-mediated events such as the inhibition of cytokine production, angiogenesis or cellular proliferation. Such compounds have utility as therapeutic agents for diseases that can be treated by the inhibition of kinase signaling pathways.

DETAILED DESCRIPTION OF THE INVENTION

In one aspect, the invention provides a compound having the Formula I:

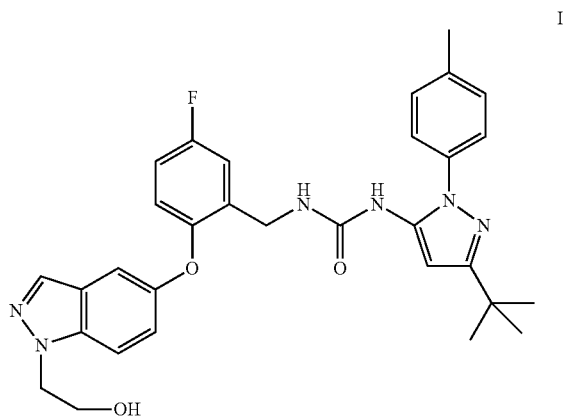

or a pharmaceutically acceptable salt thereof.

The compound may also be described by the chemical name 1-(3-tert-butyl-1-p-tolyl-1H-pyrazol-5-yl)-3-(5-fluoro-2-(1-(2-hydroxyethyl)-1H-indazol-5-yloxy)benzyl) urea.

It was found the compound of formula I has improved potency against certain kinases. In addition, it was observed that the solubility of the corresponding compound in which the N1 substituent is replaced with a phosphate ester group of formula—CH$_2$CH$_2$OPO$_3$H is several orders of magnitude greater than that of the compound of formula I. Thus, the compound of Formula I possess a unique position for creating soluble prodrugs.

More particularly, as demonstrated with test data hereinafter, the compound of formula I has been found to be a significantly more potent inhibitor of Abl and Tie2 than the compounds of Examples 94 and 138 of WO 2004/078116. Furthermore, the compounds of Examples 94 and 138 of WO 2004/078116 do not possess a primary alcohol group that can be derivatized to afford a prodrug.

In addition to compound of Formula I, the invention also includes pharmaceutically acceptable salts of the compound, and solvates of the compound and its pharmaceutically acceptable salts.

The phrase "pharmaceutically acceptable" indicates that the substance or composition is compatible chemically and/or toxicologically with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

According to another aspect, the present invention provides the use of a compound of Formula I in the manufacture of a medicament for the treatment of a kinase-mediated condition in a mammal.

In another aspect, the present invention provides a method of treating or preventing a kinase-mediated condition, comprising administering a compound of Formula I in an amount effective to treat or prevent said kinase-mediated condition.

Also provided herein are prodrugs of the compound of Formula I.

A "prodrug" is a compound that may be converted under physiological conditions or by solvolysis to the specified compound or to a salt of such compound.

The free hydroxy group of the compound of this invention may be derivatized as a prodrug by converting the hydroxy group into a group such as, but not limited to, a phosphate ester, hemisuccinate, dimethylaminoacetate, or phosphoryloxymethyloxycarbonyl group, as outlined in *Advanced Drug Delivery Reviews*, 1996, 19, 115. Carbamate prodrugs of hydroxy groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in *J. Med. Chem.*, 1996, 39, 10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate).

Therefore, according to another aspect, the present invention provides the use of a prodrug of a compound of Formula I in the manufacture of a medicament for the treatment with a compound according to claim 1 of a kinase-mediated condition in a mammal. In one embodiment, the prodrug is a phosphate prodrug.

In another aspect, the present invention provides a method of treating or preventing a kinase-mediated condition in a mammal with a compound of Formula I, comprising administering to mammal a prodrug of a compound of Formula I in an amount effective to treat or prevent said kinase-mediated condition. In one embodiment, the prodrug is a phosphate prodrug.

In accordance with another aspect, therefore, the present invention provides 2-(5-(2-((3-(3-tert-butyl-1-p-tolyl-1H-pyrazol-5-yl)ureido)-methyl)-4-fluoro-phenoxy)-1H-indazol-1-yl)ethyl dihydrogenphosphate, or a pharmaceutically acceptable salt thereof.

Without wishing to be bound by theory, it is believed that the phosphate ester compound functions as a pro-drug for the corresponding primary alcohol.

As described herein, the phosphate ester of the compound of Formula I has been found to possess particularly good solubility.

A "pharmaceutically acceptable salt," unless otherwise indicated, includes salts that retain the biological effectiveness of the corresponding free acid or base of the specified compound and are not biologically or otherwise undesirable. A compound of the invention may possess a sufficiently acidic group, a sufficiently basic group, or both functional groups, and accordingly react with any of a number of inorganic or organic bases or acids to form a pharmaceutically acceptable salt. Examples of pharmaceutically acceptable salts include those salts prepared by reaction of the compounds of this invention with a mineral or organic acid or an inorganic base, such salts including, but not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of this invention may include more than one acidic or basic moiety, the compounds of this invention may include mono, di or tri-salts in a single compound.

If the inventive compound is a base, the desired pharmaceutically acceptable salt may be prepared by any suitable method available in the art, for example, by treatment of the free base with an acidic compound, for example an inorganic acid such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, by treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

The compounds of Formula I also include other salts of such compounds that are not necessarily pharmaceutically acceptable salts, and which may be useful as intermediates for preparing and/or purifying compounds of Formula I and/or for separating enantiomers of compounds of Formula I.

This invention also embraces isotopically-labeled compounds of this invention which are identical to those recited herein, but for the fact that one or more atoms are replaced by an atom having an atomic mass or mass number different from the atomic mass or mass number usually found in nature. Isotopically labeled compounds of this invention can generally be prepared by following procedures analogous to those disclosed in the Schemes and/or in the Examples herein below, by substituting an isotopically labeled reagent for a non-isotopically labeled reagent.

Synthesis of Compounds of the Invention

The compounds of this invention may be prepared by synthetic routes that include processes analogous to those well known in the chemical arts, or as described in international patent application, publication number WO 2004/078116, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

According to another aspect, the present invention provides a process for the preparation of a compound of Formula I or a pharmaceutically acceptable salt thereof, which comprises:

(a) coupling a compound of formula II

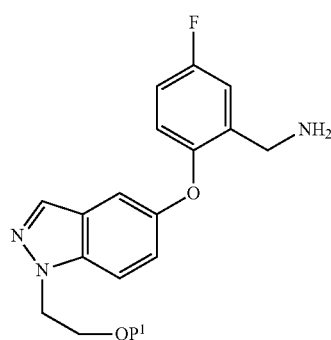

II or a salt thereof, in which $P^1$ represents a hydrogen atom or a hydroxyl protecting group, with a compound of formula III

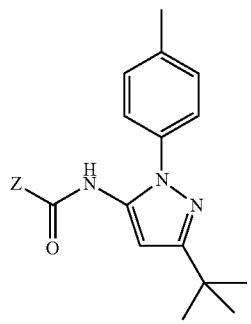

III in which Z represents a leaving group, or the corresponding isocyanate; or (b) reducing a compound of formula IV

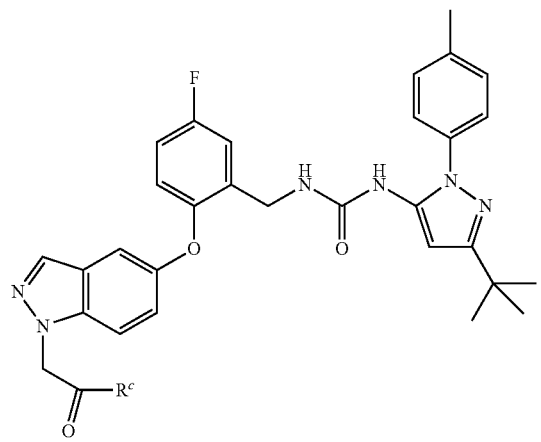

IV wherein $R^e$ represents a hydrogen atom or a residue of an alcohol;

followed by removing any protecting group and, if desired, forming a pharmaceutically acceptable salt.

Examples of convenient hydroxyl protecting groups represented by $P^1$ include cyclic hemiketals, such as tetrahydro-2H-pyran-2-yl.

The leaving group represented by Z may be, for example an unsubstituted or substituted hydrocarbyloxy group, for example a halo(1-6 C)alkoxy group, such as 2,2,2-trichloroethoxy, an alkenyloxy group such as $CH_2=C(CH_3)O-$, or an aryloxy group optionally substituted, for example, with one or more groups selected from F, Cl, Br, and $NO_2$. Particular values for an optionally substituted aryloxy group include phenoxy, 4-chlorophenoxy, 4-bromophenoxy, 4-fluorophenoxy, 4-nitrophenoxy, and 2-nitrophenoxy. In a particular embodiment, Z is phenoxy.

It has been found that compound IV can advantageously be isolated in good yield and high purity without a chromatography step when Z of compound III is an optionally substituted aryloxy group, such as a phenoxy group.

The coupling of a compound of formula (II) with a compound of formula (III) when Z is an optionally substituted phenoxy group can be conveniently performed at a temperature between 0 and 100° C., and more particularly at ambient temperature. Convenient solvents include aprotic solvents such as ethers (for example tetrahydrofuran or p-dioxane), DMF, DMSO, or acetonitrile. The coupling reaction is conveniently performed in the presence of a base such as a tertiary amine (for example, triethylamine or DMA).

Particular values of $R^e$ when represented by a residue of an alcohol include (1-6 C)alkoxy groups, such as ethoxy.

The compounds of the formulas (II) and (IV) are believed to be novel and are provided as further aspects of the invention.

The compounds of formula (III) when Z is represented by an optionally substituted aryloxy group are also believed to be novel and are provided as further aspects of the invention.

In another aspect, the present invention provides a process for preparing a phosphate prodrug of the compound of Formula I, that is, 2-(5-(2-(3-(3-tert-butyl-1-p-tolyl-1H-pyrazol-5-yl)ureido)methyl)-4-fluorophenoxy)-1H-indazol-1-yl)ethyl dihydrogenphosphate, or a pharmaceutically acceptable salt thereof, which comprises phosphorylating 1-(3-tert-butyl-1-p-tolyl-1H-pyrazol-5-yl)-3-(5-fluoro-2-(1-(2-hydroxyethyl)-1H-indazol-5-yloxy)benzyl)urea, or a salt thereof.

The phosphorylation according is conveniently performed by reacting the alcohol with a dialkyl or diaryl dialkylphosphinamidite, such as di-tert-butyl diisopropylphosphinamidite or di-phenyl diisopropylphosphinamidite, followed by removal of the alkyl or aryl groups on the phosphate product by hydrolysis or catalytic hydrogenation.

For illustrative purposes, Schemes 1 and 2 and the Examples illustrate methods for preparing the compounds of this invention as well as key intermediates. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

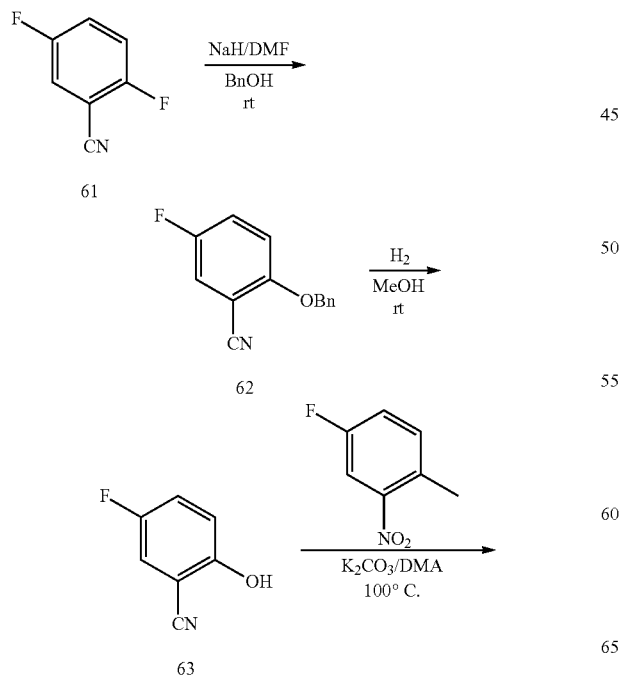

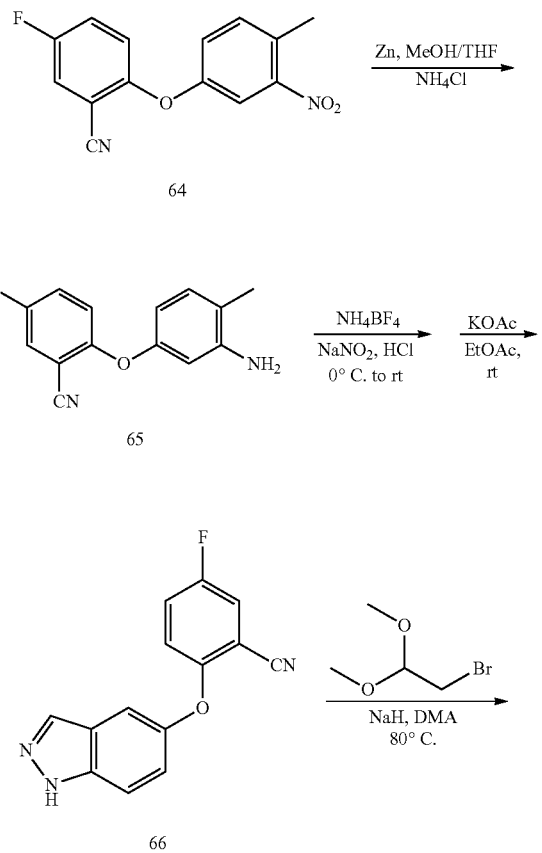

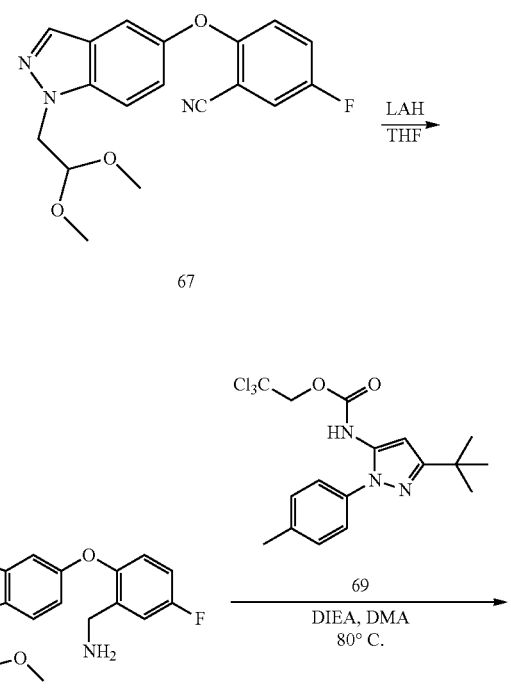

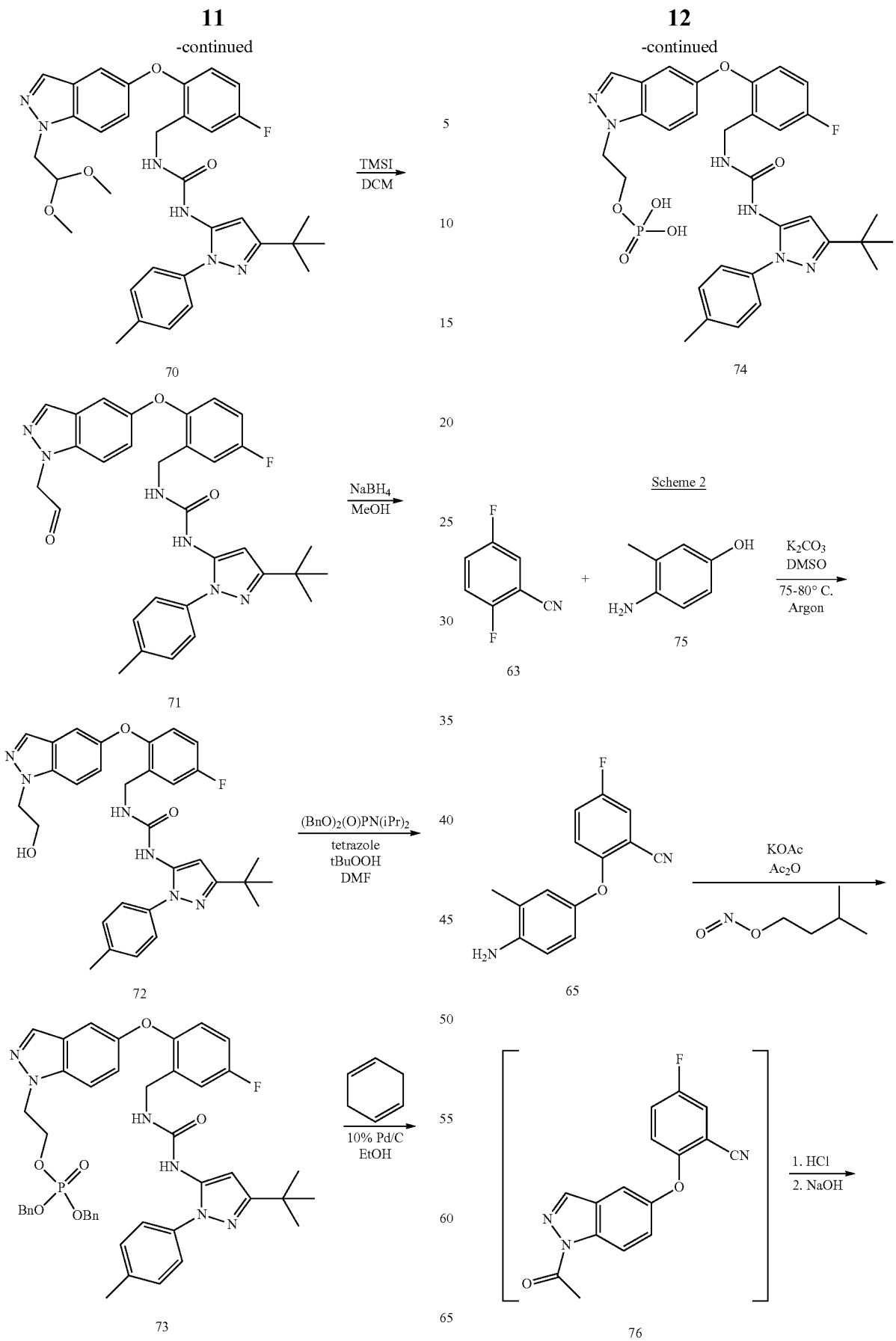

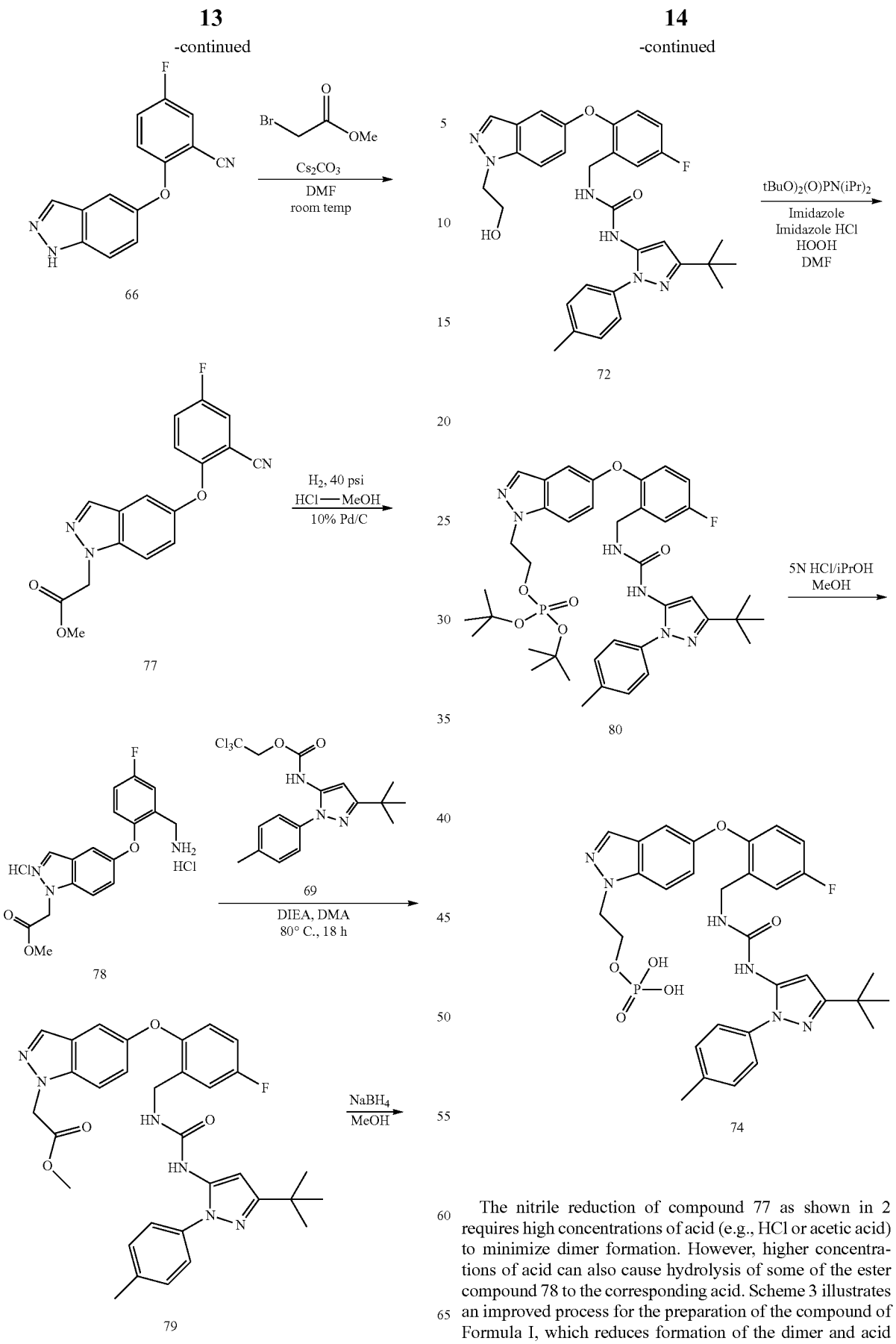

The nitrile reduction of compound 77 as shown in 2 requires high concentrations of acid (e.g., HCl or acetic acid) to minimize dimer formation. However, higher concentrations of acid can also cause hydrolysis of some of the ester compound 78 to the corresponding acid. Scheme 3 illustrates an improved process for the preparation of the compound of Formula I, which reduces formation of the dimer and acid impurities.

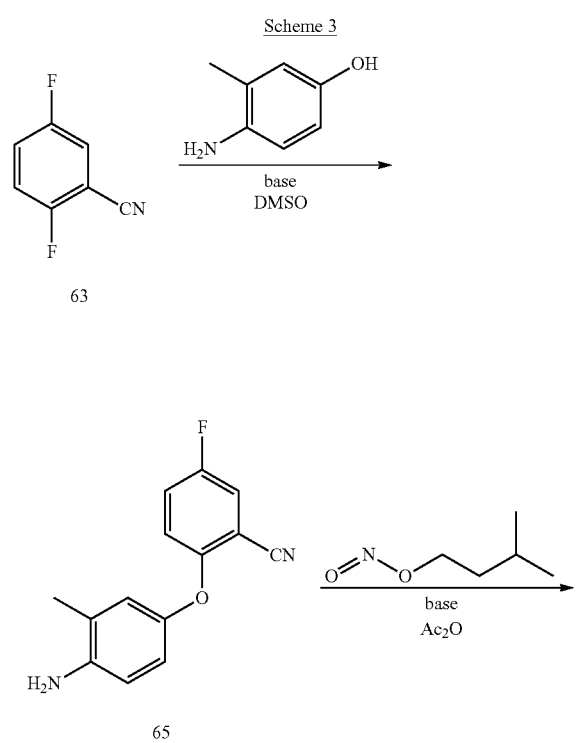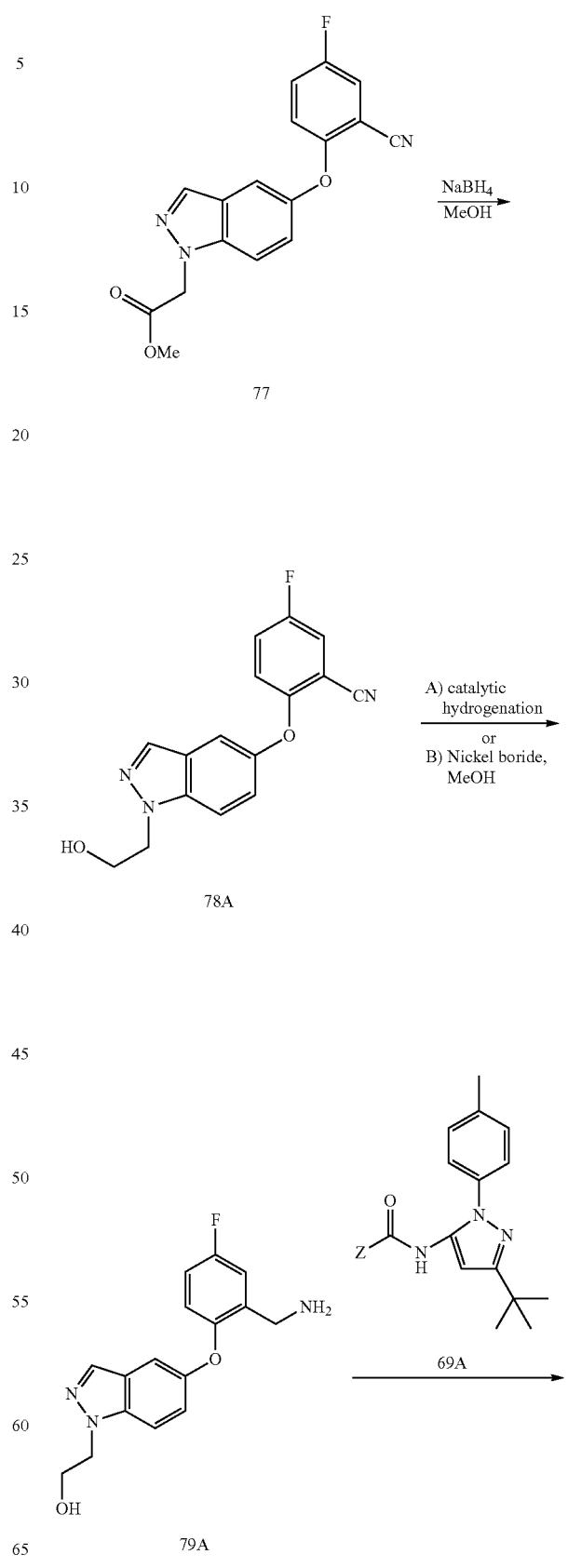

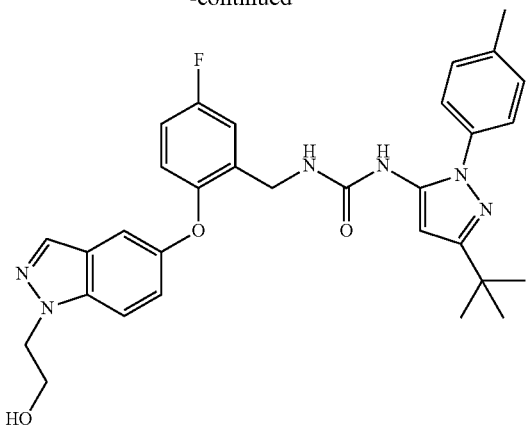

72

Scheme 3 illustrates a method of reducing the ester group of compound 77 to the corresponding alcohol prior to reduction of the nitrile group to provide compound 79A free of acid impurities and with minimum formation of dimer impurities.

More specifically, compound 77 can be reduced in a stepwise fashion, in which the ester group is reduced with sodium borohydride in a suitable solvent to provide the corresponding alcohol compound 78A. The nitrile group of compound 78A is then reduced under standard catalytic hydrogenation conditions or using nickel boride in a suitable organic solvent to provide the corresponding methyl amine compound 79A.

The route shown in Scheme 3 offers several advantages over the routes shown in Scheme 2 for the formation of the compound of Formula I. Using the routes shown in Scheme 3, the reduction of the nitrile group can be performed with higher concentrations of HCl, which advantageously lowers the amount of dimer impurity that forms. In addition, the route shown in Scheme 3 avoids the use of sodium borohydride in the final step, thereby avoiding additional purification steps to remove residual boron impurities from the final product. Therefore, by including the sodium borohydride reduction step earlier in the reaction sequence, residual boron can be easily removed during the intermediate sequence steps. In addition, the coupling of the amino alcohol compound 79A with the compound 69A can be performed at lower temperatures, thus improving the purity of the product 72. Accordingly, the route shown in Scheme 3 enables improved throughput for the synthesis of the compound of Formula I, and consequently provides an efficient synthetic route for the production of the compound f Formula I that is more amenable to or suitable for large-scale manufacture.

Accordingly, also provided is a process for preparing a compound of formula (II), comprising:

(i) reducing a compound of formula (V)

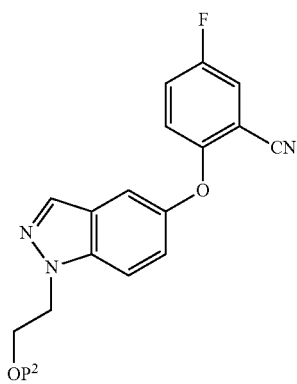

(V)

in which $P^2$ represents hydrogen or a hydroxyl protecting group, under catalytic hydrogenation conditions or in the presence of nickel boride Referring to step (i), hydrogenation catalysts include any suitable palladium catalyst, such as $Pd(OH)_2$ or palladium supported on carbon. The hydrogenation takes place under acidic conditions (such as by the addition of an acid, for example HCl or acetic acid) or with the addition of ammonia. The catalytic hydrogenation can be carried out in any suitable solvent system such as an alcohol (e.g., methanol, ethanol, isopropanol), ester (e.g., ethyl acetate) or ether (e.g., THF). Mixed solvents, for example alcohol and THF, are also suitable for the hydrogenation step. Hydrogen pressure can be in the range between 25 to 100 psi, for example 40 psi. The reduction is typically performed at a temperature between 20-100° C.

Referring to step (i), the nickel boride can be prepared in situ from a transition metal salt, preferably a Ni(II) salt, and sodium borohydride. In a preferred embodiment, the nickel boride is prepared from nickel (II) chloride and sodium borohydride. The reaction is conveniently performed in a suitable solvent such as an alcohol (e.g., methanol, ethanol, isopropanol). The reduction is typically performed at ambient temperature.

A compound of formula (V) can be prepared by reducing a compound of formula (VI)

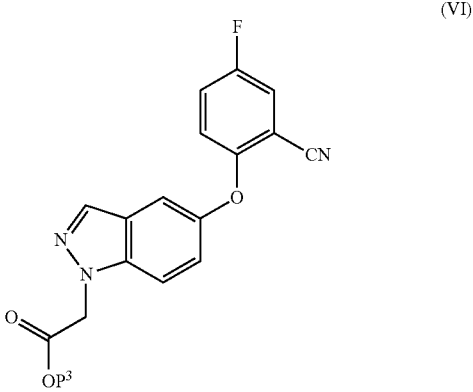

(VI)

wherein $P^3$ is as defined for $P^2$, using any convenient ester reducing conditions (e.g., sodium borohydride), in a suitable solvent such as an alcohol (e.g., methanol, ethanol, isopropanol).

In preparing compounds of this invention, protection of remote functionalities (e.g., primary or secondary amines, alcohols, etc.) of intermediates may be necessary. The need for such protection will vary depending on the nature of the remote functionality and the conditions of the preparation methods. For example, suitable amino-protecting groups (NH-Pg) include acetyl, trifluoroacetyl, t-butoxycarbonyl (BOC), benzyloxycarbonyl (CBz) and 9-fluorenylmethylenoxycarbonyl (Fmoc). Convenient hydroxyl protecting groups include tetrahydro-2H-pyran-2-yl, benzyl, trialkylsilyl, and acetal. The need for such protection is readily determined by one skilled in the art. For a general description of protecting groups and their use, see T. W. Greene, Protective Groups in Organic Synthesis, John Wiley & Sons, New York, 1991.

Methods of Treatment

The compounds of the invention may be used to treat diseases mediated by modulation or regulation of protein kinases. Accordingly, another aspect of the invention provides methods of treating or preventing diseases or conditions described herein by administering to a mammal, such as a human, a therapeutically effective amount of a compound of this invention or solvate, metabolite, or pharmaceutically acceptable salt thereof, in an amount effective to treat or prevent said disorder. In one embodiment, the method comprises administering to a mammal a compound of this invention in an amount effective to inhibit one or more kinases.

An "effective amount" refers to an amount of compound that, when administered to a mammal in need of such treatment, is sufficient to effect treatment for a disease mediated by the activity of one or more protein kinases, such as p38 MAPK, and the associated kinase-mediated events such as cytokine production. Thus, for example, a therapeutically effective amount of a compound of this invention or a salt, active metabolite thereof, is a quantity sufficient to modulate, regulate, or inhibit the activity of one or more protein kinases such that a disease condition which is mediated by that activity is reduced or alleviated.

"Treating" is intended to mean at least the mitigation of a disease condition in a mammal, such as a human, that is affected, at least in part, by the activity of one or more protein kinases. The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The amount of a compound of this invention administered to a mammal will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

In one aspect of this invention, the compounds of this invention or pharmaceutical salts thereof may be formulated into pharmaceutical compositions for administration to animals or humans to treat or prevent a kinase-mediated condition. The term "kinase-mediated condition" as used herein means any disease or other deleterious condition in which p38 is known to play a role, and includes conditions that are known to be caused by IL-1, TNF, IL-6 or IL-8 overproduction. Such conditions include, but are not limited to, inflammatory diseases, autoimmune diseases, destructive bone disorders, proliferative disorders, infectious diseases, viral disease, fibrotic disease and neurodegenerative diseases.

Inflammatory diseases which may be treated or prevented include, but are not limited to, acute pancreatitis, chronic pancreatitis, asthma, allergies, and adult respiratory distress syndrome.

Autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented include, but are not limited to, osteoporosis, osteoarthritis and multiple myeloma-related bone disorder.

Fibrotic diseases which may be treated or prevented include, but are not limited to, idiopathic pulmonary fibrosis, kidney and liver fibrosis.

Proliferative diseases which may be treated or prevented include, but are not limited to, acute myelogenous leukemia, chronic myelogenous leukemia, metastatic melanoma, Kaposi's sarcoma, myelodysplastic syndrome, multiple myeloma, astrocytoma, bone cancer, brain cancer, breast cancer, colorectal cancer, gastric cancer, glioma, glioblastoma, multiforme, head and neck cancer, hematological cancer, hematopoiesis disorders, interstitial lung diseases, kaposi's sarcoma, lymphocytic leukemia, melanoma, myeloid leukemia, non-small cell lung cancer, ovarian cancer, prostate cancer, sarcoma, skin cancer, small cell lung cancer, and stomach cancer. Other patients which can be treated include those undergoing bone marrow transplantation.

Infectious diseases which may be treated or prevented include, but are not limited to, sepsis, septic shock, and Shigellosis.

Viral diseases which may be treated or prevented include, but are not limited to, acute hepatitis infection (including hepatitis A, hepatitis B and hepatitis C), HIV infection and CMV retinitis.

Degenerative conditions or diseases which may be treated or prevented by the compounds of this invention include, but are not limited to, Alzheimer's disease, Parkinson's disease, cerebral ischemia and other neurodegenerative diseases.

The term "kinase-mediated conditions" also includes ischemia/reperfusion in stroke, heart attacks, myocardial ischemia, organ hypoxia, vascular hyperplasia, cardiac hypertrophy and thrombin-induced platelet aggregation.

In addition, the kinase inhibitors of this invention are also useful for inhibiting the expression of inducible pro-inflammatory proteins such as prostaglandin endoperoxide synthase-2 (PGHS-2), also referred to as cyclooxygenase-2 (COX-2). Therefore, other "kinase-mediated conditions" include, but are not limited to, edema, analgesia, fever and pain, such as neuromuscular pain, headache, cancer pain, dental pain and arthritis pain.

The conditions and diseases that may be treated or prevented by the kinase inhibitors of this invention may also be conveniently grouped by the cytokine (e.g., IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, rubella arthritis, acute synovitis, diabetes, pancreatic β-cell disease and Alzheimer's disease.

TNF-mediated diseases or conditions include, but are not limited to, rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and veterinary viral infections, such as lentivirus infections, including, but not limited to equine infectious anaemia virus, caprine arthritis virus, visna virus or maedi virus; or retrovirus infections, including feline immunodeficiency virus, bovine immunodeficiency virus, or canine immunodeficiency virus.

IL-8 mediated diseases or conditions include, but are not limited to, diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds of this infection may be used topically to treat or prevent conditions caused or exacerbated by IL-1 or TNF. Such conditions include, but are not limited to, inflamed joints, eczema, psoriasis, inflammatory skin conditions such as sunburn, inflammatory eye conditions such as conjunctivitis, pyresis, pain and other conditions associated with inflammation.

Although the compounds of this invention are primarily of value as therapeutic agents for use in warm-blooded animals (including humans), they are also useful whenever it is required to inhibit the effects of cytokines. Thus, they are useful as pharmacological standards for use in the development of new biological tests and in the search for new pharmacological agents.

The size of the dose for therapeutic or prophylactic purposes of a compound of this invention will naturally vary according to the nature and severity of the conditions, the age and sex of the animal or patient and the route of administration, according to well known principles of medicine.

Another aspect of this invention provides a compound of this invention for use as a medicament in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Combination Therapy

The compounds of this invention may be used in combination with other drugs and therapies used in the treatment of disease states which would benefit from the inhibition of kinases and the associated cytokines, such as IL-1, TNF, IL-6 or IL-8. The dose of the second drug can be appropriately selected based on a clinically employed dose. The proportion of the compound of this invention and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the compound of this invention.

The second drug of the pharmaceutical combination formulation or dosing regimen has, for example, complementary activities to the compound of this invention such that they do not adversely affect each other. Such drugs are suitably present in combination in amounts that are effective for the purpose intended. Accordingly, another aspect of this invention provides a composition comprising a compound of this invention in combination with a second drug, such as described herein.

The compound of this invention and the additional pharmaceutically active drug(s) may be administered together in a unitary pharmaceutical composition or separately and, when administered separately this may occur simultaneously or sequentially in any order. Such sequential administration may be close in time or remote in time. The amounts of the compound of this invention and the second drug(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when a compound of this invention and the second drug are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when a compound of this invention and the second drug are administered or delivered sequentially, e.g., by different injections in separate syringes. For example, during alternation therapy, an effective dosage of each active ingredient can be administered sequentially, i.e., serially, whereas in combination therapy, effective dosages of two or more active ingredients are administered together.

For example, by virtue of their ability to inhibit cytokines, the compounds of this invention are of value in the treatment of certain inflammatory and non-inflammatory diseases which are currently treated with a cyclooxygenase-inhibitory non-steroidal anti-inflammatory drug (NSAID) such as indomethacin ketorolac, acetylsalicylic acid, ibuprofen, sulindac, tolmetin and piroxicam. Co-administration of a compound of this invention with a NSAID can result in a reduction of the quantity of the latter agent needed to produce a therapeutic effect, and thus the likelihood of adverse side-effects from the NSAID such as gastrointestinal effects are reduced. Thus according to a further feature of the invention there is provided a pharmaceutical composition which comprises a compound of this invention, or a pharmaceutically-acceptable salt thereof, in conjunction or admixture with a cyclooxygenase inhibitory non-steroidal anti-inflammatory agent, and a pharmaceutically-acceptable diluent or carrier.

The compounds of this invention may also be used in the treatment of conditions such as rheumatoid arthritis in combination with anti-arthritic agents such as gold, methotrexate, steroids and pencillinamine, and in conditions such as osteoarthritis in combination with steroids.

The compounds of this invention may also be used in the treatment of degradative diseases, for example osteoarthritis, in combination with chondroprotective, anti-degradative and/or reparative agents such as Diacerhein, hyaluronic acid formulations such as Hyalan, Rumalon, Arteparon and glucosamine salts such as Antril.

The compounds of this invention may also be used in the treatment of asthma in combination with anti-asthmatic agents such as bronchodilators and leukotriene antagonists.

Administration of Compounds of the Invention

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. It will be appreciated that the route used may vary with, for example, the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

The pharmaceutical compositions of the invention are formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the compound to be administered will be governed by such considerations, and is the minimum amount necessary to prevent, ameliorate, or treat the disorder. The compound of this invention is typically formulated into pharmaceutical dosage forms to provide an easily controllable dosage of the drug and to enable patient compliance with the prescribed regimen.

The composition for use herein is preferably sterile. In particular, formulations to be used for in vivo administration must be sterile. Such sterilization is readily accomplished, for example, by filtration through sterile filtration membranes. The compound ordinarily can be stored as a solid composition, a lyophilized formulation or as an aqueous solution.

Pharmaceutical formulations of the compounds of this invention may be prepared for various routes and types of administration. For example, a compound of this invention having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, a milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range for example from about 3 to about 8. Formulation in an acetate buffer at pH 5 is a suitable embodiment. The formulations may be prepared using conventional dissolution and mixing procedures. For example, the bulk drug substance (i.e., compound of this invention or stabilized form of the compound (e.g., complex with a cyclodextrin derivative or other known complexation agent) is dissolved in a suitable solvent in the presence of one or more excipients.

The particular carrier, diluent or excipient used will depend upon the means and purpose for which the compound of this invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The formulations may also include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of this invention or pharmaceutical composition thereof) or aid in the manufacturing of the pharmaceutical product (i.e., medicament). The active pharmaceutical ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes.

Sustained-release preparations of compounds of this invention may be prepared. Suitable examples of sustained-release preparations include semipermeable matrices of solid hydrophobic polymers containing a compound of this invention, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

The pharmaceutical compositions of this invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Pharmaceutical compositions of this invention suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compositions of the invention may also be formulated in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder)

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be formulated in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols. Formulations suitable for vaginal administration may be presented as pessaries, tampons, creams, gels, pastes, foams or spray formulations containing in addition to the active ingredient such carriers as are known in the art to be appropriate.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for transdermal administration may be in the form of those transdermal skin patches that are well known to those of ordinary skill in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

The pharmaceutical composition (or formulation) for application may be packaged in a variety of ways depending upon the method used for administering the drug. For example, an article for distribution can include a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The formulations may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. In one embodiment, a suitable amount of a compound of this invention is administered to a mammal in need thereof. Administration in one embodiment occurs in an amount between about 0.001 mg/kg of body weight to about 60 mg/kg of body weight per day. In another embodiment, administration occurs in an amount between 0.5 mg/kg of body weight to about 40 mg/kg of body weight per day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

Articles of Manufacture

In another embodiment of the invention, an article of manufacture, or "kit", containing materials useful for the treatment of the disorders described above is provided. In one embodiment, the kit comprises a container comprising a compound of this invention. Suitable containers include, for example, bottles, vials, syringes, blister pack, etc. The container may be formed from a variety of materials such as glass or plastic. The container may hold a compound of this invention or a formulation thereof which is effective for treating the condition and may have a sterile access port (for example, the container may be an intravenous solution bag or a vial having a stopper pierceable by a hypodermic injection needle).

The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. In one embodiment, the label or package inserts indicates that the composition comprising a compound of this invention can be used to treat a kinase-mediated disease or disorder. The label or package insert may also indicate that the composition can be used to treat other disorders.

In certain embodiments, the kits are suitable for the delivery of solid oral forms of a compound of this invention, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to another embodiment, a kit may comprise (a) a first container with a compound of this invention contained therein; and (b) a second container with a second pharmaceutical formulation contained therein, wherein the second pharmaceutical formulation comprises a second compound useful for treating a kinase-mediated disease or disorder. Alternatively, or additionally, the kit may further comprise a third container comprising a pharmaceutically-acceptable buffer, such as bacteriostatic water for injection (BWFI), phosphate-buffered saline, Ringer's solution and dextrose solution. The kit may further include other materials desirable from a commercial and user standpoint, including other buffers, diluents, filters, needles, and syringes.

The kit may further comprise directions for the administration of the compound of this invention and, if present, the second pharmaceutical formulation. For example, if the kit comprises a first composition comprising a compound of this invention and a second pharmaceutical formulation, the kit may further comprise directions for the simultaneous, sequential or separate administration of the first and second pharmaceutical compositions to a patient in need thereof.

In certain other embodiments wherein the kit comprises a composition of this invention and a second pharmaceutical formulation, the kit may comprise a container for containing the separate compositions such as a divided bottle or a divided foil packet, however, the separate compositions may also be contained within a single, undivided container. In certain embodiments, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Biological Activity p38 MAPK Inhibition

The activity of the compounds of this invention may be assayed for p38 MAPK inhibition in vitro, in vivo, or in a cell line. In vitro assays include assays that determine inhibition of either the kinase activity or ATPase activity of activated p38 MAPK. Alternate in vitro assays quantitate the ability of the inhibitor to bind to p38 MAPK and may be measured either by radiolabelling the inhibitor prior to binding, isolating the inhibitor/p38 MAPK complex and determining the amount of radiolabel bound, or by running a competition experiment where new inhibitors are incubated with p38 MAPK bound to known radioligands. These and other useful in vitro and cell culture assays are well known to those of skill in the art.

Cell culture assays of the inhibitory effect of the compounds of this invention may be used to determine the amounts of TNF-α, IL-1, IL-6 or IL-8 produced in whole blood or cell fractions thereof in cells treated with inhibitor as compared to cells treated with negative controls. Level of these cytokines may be determined through the use of commercially available ELISAs or as described in the Biological Examples section below.

EXAMPLES

In order to illustrate the invention, the following examples are included. However, it is to be understood that these examples do not limit the invention and are only meant to suggest a method of practicing the invention.

Biological Examples

The biological activities of the compounds of the invention were demonstrated by the following in vitro assays. Compounds used in Examples C-M were: Compound 72: 1-(3-tert-butyl-1-p-tolyl-1H-pyrazol-5-yl)-3-(5-fluoro-2-(1-(2-hydroxyethyl)-1H-indazol-5-yloxy)benzyl)urea (Examples 1 and 3); and Compound 74: 2-(5-(2-(3-(3-tert-butyl-1-p-tolyl-1H-pyrazol-5-yl)ureido)methyl)-4-fluorophenoxy)-1H-indazol-1-yl)ethyl dihydrogenphosphate (Examples 2 and 4).

Example A p38 Biochemical Assay p38 activity was assayed at room temperature in a 100 μL reaction containing 5 nM activated p38α enzyme and 1 μM ATF-2 (Activating Transcription Factor 2 fusion protein) as the substrate in 25 mM HEPES (pH 7.4), 100 μM Vanadate, 1 mM DTT, 10 mM MgCl$_2$ and 10 μM [γ-$^{33}$P]-ATP (~0.1 μCi P$^{33}$/reaction). The reaction was terminated after 30-40 minutes by adding 25% TCA, allowed to stand for 5 minutes, and then transferred directly to a GF-B membrane filter plate. The filter was washed twice for 30 seconds with 0.5% phosphoric acid using a Tomtec Mach III Automated Harvestor. After washing, the vacuum was continued for 30 seconds to dry the filter. Approximately 30 μL of scintillant was added per well to the filter plate and then read in a Liquid Scintillation Counter (Packard TopCount HTS).

Example B

PBMC Assay

The ability of compounds of this invention to inhibit TNF-α production was assessed by using human peripheral blood mononuclear cells ("PBMC") which synthesize and secrete TNF-α when stimulated with lipopolysaccharide.

Compound test solutions were made by making 5 fold serial dilutions in DMSO, which dilutions were then diluted to 5× stocks by diluting with MEM, 2% heat inactivated fetal bovine serum ("FBS"), 20 mM HEPES, 2 mM L-glutamine, and 1% penicillin/streptomycin.

PBMC's were isolated from human blood as follows. Whole blood samples were collected from human volunteers into Vacutainer™ CPT from Becton Dickinson. Tubes were mixed and centrifuged at room temperature (18-25° C.) in a horizontal rotor for a minimum of 15 minutes at 1500-1800 RCF (relative centrifugal force). For each donor, the buffy coat layers were pooled into a single tube and washed twice with phosphate buffered saline ("PBS"). The cell pellet was resuspended in MEM, 2% heat inactivated fetal bovine serum ("FBS"), 20 mM HEPES, 2 mM L-glutamine, and 1% penicillin/streptomycin. Total cell number was determined using a hemocytometer and the cell suspension was adjusted to 2×106 cells/mL.

To each well of a 96-well cell culture plate was added 0.1 mL of cell suspension. A compound test solution (30 μL) was added, and the cells were incubated in a 37° C./5% CO$_2$ incubator for 1 hour, and then 20 μL of 7.5 ng/mL lipopolysaccharide (LPS E. Coli K-235) was added to each well, and the cells were returned to the 37° C./5% CO$_2$ incubator for 16-20 hours. The cells were centrifuged for 15 minutes at 1100 RCF. Approximately 0.12 mL of the supernatant was transferred into a clean 96 well polypropylene plate. The samples were either assayed immediately or were stored at −80° C. until ready for assay. TNF-α levels were determined in each sample using a human TNF-a ELISA assay such as that described below.

TNF-α levels were determined using the following assay. TNF-alpha antibody coated plates were prepared by adding 150 μL of 2 μg/mL anti-TNF-α purified mouse monoclonal IgG in Carbonate-Bicarbonate buffer (BupH™ Carbonate-Bicarbonate Buffer Pack) to wells of a 96-well Immulon 4 plate (Immulon 4 ELISA Flat Bottom Plate; Dynex, catalog number 011-010-3855) and incubated overnight at 2-8° C. Coating solution was removed and 200 μL of blocking buffer (20 mM HEPES pH 7.4, 150 mM NaCl, 2% BSA) was added and plates were stored 2-8° C. until ready to use. A ten-point recombinant human TNF-α standard curve was prepared by a 1:2 serial dilution in sample diluent (20 mM HEPES, pH 7.4, 150 mM NaCl, 2 mM MgCl$_2$, 1% BSA) with a top concentration of 6000 pg/mL.

Blocking solution was removed from TNF-α ELISA plates by washing five times with 300 μL of "wash buffer" (20 mM HEPES, pH 7.4, 150 mM NaCl, 2 mM MgCl$_2$, 0.02% Tween-20). 50 μL of sample diluent was added to all wells, and then either 50 μL of a TNF-α standard curve solution or test compound supernatant was added to all wells. The plate was incubated at room temperature for one hour with shaking (300 rpm). The plate was washed wash five times with 300 μL wash buffer. 100 μL of 0.2 μg/mL biotinylated goat anti-human TNF-a in "antibody diluent" (20 mM HEPES, pH 7.4, 150 mM NaCl, 2 mM MgCl$_2$, 1% BSA, 0.02% Tween-20) was added per well, and the plate was incubated at room temperature for one hour with shaking (300 rpm). The plate was washed wash five times with 300 μL wash buffer per well. 100 μL of 0.02 μg/mL streptavidin alkaline phosphatase in antibody diluent was added per well, and the plate was incubated at room temperature for one hour with shaking (300 rpm). The plate was washed wash five times with 300 μL wash buffer per well. 200 μL of 1 mg/mL pNPP (p-nitrophenyl phosphate) in diethanolamine buffer with 0.5 mM MgCl$_2$ was added per well, and the plate was incubated for 30 to 45 minutes at room temperature with shaking (300 rpm). Reaction progress was monitored by determining optical density: when the top standard reached an OD between 2.0 and 3.0, 50 μL of 2N NaOH was added per well. The optical density of each well was determined within 30 minutes, using a microtiter plate reader set to 405 nm. The data was analyzed in XL fit using 4-parameter curve fitting.

The following reagents were used in the above-described assays. Dulbecco's Phosphate Buffered Saline without Calcium or Magnesium (Gibco Catalog Number 14190); Minimum essential medium Eagle (MEM; Gibco Catalog Number 11090); penicillin-streptomycin (Gibco Catalog Number 15140); L-glutamine, 200 mM (Gibco Catalog Number 25030); HEPES, 1M (Gibco Catalog Number 15630); fetal bovine serum ("FBS"; HyClone Catalog Number SH30070.03); lipopolysaccharides from Escherichia coli K-235 ("LPS"; Sigma Catalog Number L2018); anti-TNF-α, Purified Mouse Monoclonal IgG (R&D Systems Catalog Number MAB210); BupH™ Carbonate-Bicarbonate Buffer Pack (Pierce Catalog Number 28382); HEPES (FW 238.3; Sigma Catalog Number H3575); NaCl (Sigma Catalog Number S7653); bovine serum albumin ("BSA"; Jackson ImmunoReseach Catalog Number 001-000-162); polyoxyethylene 20 sorbitan monolaurate (Sigma Catalog Number P2287); magnesium chloride, hexahydrate (Sigma Catalog Number M2670); recombinant human TNF-α (R&D Systems Catalog Number 210TA010); biotinylated TNF-a affinity purified goat IgG (R&D Systems Catalog Number BAF210); streptavidin alkaline phosphatase (Jackson ImmunoResearch Catalog Number 016-050-084); diethanolamine Substrate Buffer (Pierce Catalog Number 34064); p-nitrophenyl phosphate (Sigma Catalog Number N2765).

Example C

Activity of Compound 72 Against Various Kinases

The p38α activity of Compound 72 employing an in-house p38α radioactive kinase assay using ATF-2 as a substrate was explored. The selectivity of Compound 72 was determined by assaying the activity of 202 protein kinases in the presence of 1 μM Compound 72. $IC_{50}$ determinations were subsequently run for those kinases inhibited by >80% in the initial screen (ATP concentration at $K_m$) per established protocols.

As shown in Table 1, Compound 72 is a potent inhibitor of p38α Abelson cytoplasmic tyrosine kinase (Abl), Abelson-related gene (Arg) and the Tie-2 receptor tyrosine kinase. In addition to these activities, Compound 72 is also moderately potent against the Imatinib-resistant form of BCR-Abl T315I, the src-family tyrosine kinases Hck, Lyn and Fyn, and the receptor tyrosine kinases FGFR1 (fibroblast growth factor receptor 1; FGFR1) and VEGFR2 (vascular endothelial growth factor receptor 2; KDR).

TABLE 1

| Kinase | $IC_{50}$ |
| --- | --- |
| p38α | <2 nM |
| Abl | 4 nM |
| Arg | 10 nM |
| Tie2 | 1 nM |
| Abl (T315I) | 68 nM |
| Hck | 26 nM |
| Lyn | 25 nM |
| Fyn | 41 nM |
| FGFR1 | 28 nM |
| VEGFR | 74 nM |

By way of comparison, the compounds of Examples 94 and 138 of WO 2004/078116 were also tested.

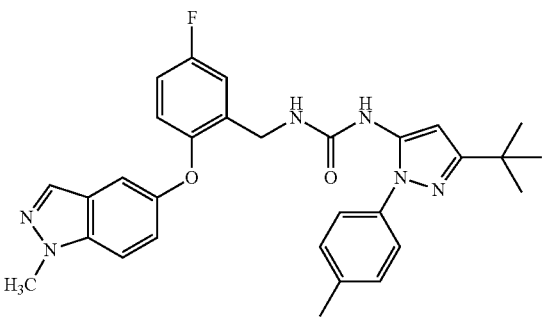

Example 94

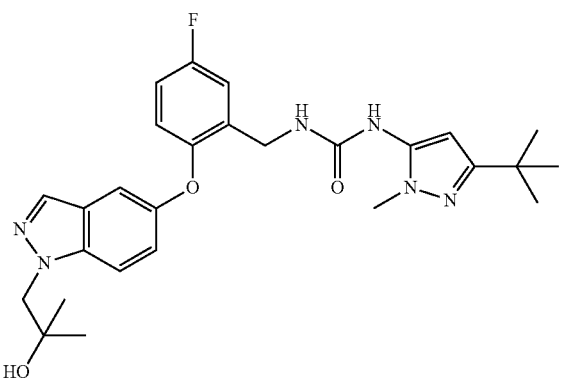

Example 138

The results are provided in Table 1a below.

TABLE 1a

| Kinase | Example 94 $IC_{50}$ | Example 138 $IC_{50}$ |
| --- | --- | --- |
| P38α | <2 nM | <2 nM |
| Abl | 10 nM | >500 nM |
| Tie2 | 4 nM | >500 nM |

The results show that compound 72 is a significantly more potent inhibitor of Abl and Tie2 than the compounds of Examples 94 and 138 of WO 2004/078116.

Example D

Cell Activity of Compound 72 Against the p38 Pathway

HeLa cells were treated with Compound 72 for 60 minutes prior to stimulation with 1 μg/mL anisomycin for 60 minutes to induce activation of p38 pathway. Cells were labeled with antibodies against the phosphorylated form of HSP27 (Ser78) and GAPDH as a normalization control. Cells were imaged and quantified using a LI-COR Aeriustm imager.

The results demonstrated that Compound 72 is a potent inhibitor of the p38 pathway in cells, with an apparent $IC_{50}$ of 2 nM. In a functional cell assay, this compound was also tested for its ability to inhibit TNF-α production in whole blood treated with bacterial lipopolysaccharide (LPS) to induce cytokine production (as detected by ELISA), generating an apparent $IC_{50}$ of 30 nM.

Example E

Cell Activity of Compound 72 Against Tie2 Receptor

For the time course experiment, HUVECs were serum-starved for 2 hours then stimulated with 200 ng/mL the Tie2 receptor agonist Angiopoietin-1 (Ang-1). Cells were harvested at the indicated time points and immunoblotted with antibodies against phospho-AKT, phospho-Erk, phospho-HSP27, phospho-p38 and GAPDH. Signals were quantified and normalized to GAPDH to assess extent of induction as a result of Tie2 receptor activation. The results were demonstrated as an immunoblot and graph showing the time course of Erk, AKT and p38 pathway activation in response to the Tie2 receptor agonist Ang-1 in human umbilical vascular endothelial cells (HUVECs). The results show that only the AKT and Erk pathways are activated in response to Tie2 receptor activation.

For the Tie2 activation study, HUVECs were serum-starved for 2 hours then treated with varying concentrations of Compound 72 for 60 minutes prior to stimulation with 200 ng/mL Ang-1 for 10 minutes. Tie2 was then immunopurified (IP) and immunoblotted with anti-phosphotyrosine (pTyr) and anti-Tie2 antibodies to assess the degree of Tie2 autophosphorylation. Lysates were immunoblotted with anti-phospho-Erk and anti-phospho-AKT (Ser473) antibodies, respectively. Signals were quantified and normalized to GAPDH as a loading control. The results were shown in an immunoblot and a graph. Compound 72 treatment results in a dose-dependent inhibition of both Tie2 autophosphorylation as well as its downstream effectors Erk and AKT with an $IC_{50}$ of <33 nM for the former and <11 nM for the latter.

Example F

Cell Activity of Compound 72 Against BCR-Abl

The BCR-Abl positive chronic myelogenous leukemia cell line K562 was treated with various concentrations of Imatinib or Compound 72 as indicated for 72 hours at 37° C., 5% $CO_2$. Cell viability was subsequently measured using CellTiter Blue (Promega) to determine $IC_{50}$ values for each compound. The $IC_{50}$ values determined were 278 nM and 62 nM for Imatinib and Compound 72, respectively.

Extracts of K562 cells treated with varying concentrations of either Imatinib or Compound 72 for 2 hours at 37° C., 5% $CO_2$ were prepared and immunoblotted for autophosphorylated Abl (p-Abl, Tyr245) and Abl substrates STATS (pSTAT5, Tyr694) and CrkL (pCrkL, Tyr207). The results show that Compound 72 is greater than four times more potent than Imatinib at inhibiting proliferation in the BCR-Abl driven cell line K562. The results of immunoblotting of K562 extracts treated with pBCR-Abl, pSTAT5, pCrkL or GAPDH at the concentrations 5000, 1000, 333, 111, 37 and 0 nM Imatinib or Compound 72 were measured. This assay shows that both Compound 72 and Imatinib are capable of inhibiting the autophosphorylation of the BCR-Abl as well as its substrates STATS and CrkL. Compound 72, in accordance with the proliferation data, is more potent at inhibiting the phosphorylation of these substrates.

Example G

Physical Properties, Metabolic Profile and Safety Profile of Compounds 72 and 74

1. Solubility Determination

The results of the solubility determination are shown in Table 2.

TABLE 2

| Solubility | |
| --- | --- |
| Compound 72 | Compound 74 (Prodrug) |
| pH 3.0 <0.005 mg/mL | pH 1.2 <1 mg/mL |
| pH 7.4 <0.005 mg/mL | pH 6.5 >1000 mg/mL |
|  | pH 7.4 ~940 mg/mL |

By way of comparison, the solubilities of the compounds of Examples 94 and 138 of WO 2004/078116 were found to be <0.001 mg/mL at pH 6.5 and 7.4.

2. CYP Inhibition Assays (Fluorescent, LC-MS)

$IC_{50}$ values for CYP3A4, CYP2 C19 and CYP2 C9 were derived by measuring the ratio of the formation of metabolite of a specific substrate to internal standard compared to control by liquid chromatography/mass spectrometry (LC/MS) using pooled human liver microsomes (n=1). $IC_{50}$ values for CYP2D6 and CYP1A2 were derived by measuring the relative fluorescence compared to control of commercially available P450-isoform-specific fluorescent probes and recombinant protein (n=1). The results are shown in Table 3.

TABLE 3

| CYP Inhibition Profile (Compound 72) | |
| --- | --- |
| | $IC_{50}$ |
| CYP3A4 | Midazolam: ~8 μM |
|  | Testosterone: ~10 μM |
| CYP2D6 | 3 μM |
| CYP2C9 | 5 μM (LC/MS) |
| CYPC19 | 25 μM (LC/MS) |
| CYP1A2 | 25 μM |

3. Off-target Toxicity Assays

Compound 72 was assayed for binding (ligand displacement assay) at 10 μM against the following panel of 28 receptors, ion channels and transporters.

Of the 28 molecular entities screened, only the sodium channel (site 2) was shown to significantly interact (>50% displacement) with the compound.

4. Safety Assessment Assays hERG assay was performed using a standard patch clamp protocol. AMES assay (bacterial reverse mutation assay) was performed according to protocol. Compound 72 was tested at 0.5-5000 μg/test plate with/without S9 activation. In vitro and in vivo micronucleus assays were performed according to protocol. The results are shown in Table 4.

TABLE 4

| Safety | |
| --- | --- |
| Assay | Compound 72 |
| hERG Patch Clamp | 64% Inhibition at 10 μM |
| AMES mutagenicity | Negative |
| Micronucleus (in vitro) | Negative |

5. Tolerability Study

Mice (strain CD-1, n=5 per dose group) were dosed with Compound 72 (as Compound 74) at 10, 30 or 100 mg/kg BID for 14 days. Weight loss was assessed throughout study. Blood was removed on the final day for clinical chemistries (albumin, alkaline phosphatase, ALT, Amylase, BUN, calcium, cholesterol, creatinine, glucose, phosphate, total bilirubin, TP, Globulin). The results are shown in Table 5. No compound-related mortalities were observed. In this study, even at 100 mg/kg, no dose-limiting toxicities (DLTs) were seen and therefore a maximum tolerated dose (MTD) was not identified.

TABLE 5

Tolerability (in vivo)

| | |
|---|---|
| Species | Mouse (CD-1) |
| Dosing | 10, 30 and 100 mg/kg BID |
| Study duration | 14 days |
| Weight loss | <5% (all dose groups) |
| Clinical chemistries | Within normal range (all dose groups) |
| Comments: | No compound-related mortalities |
| | no observed DLTs |
| | MTD not achieved |

Example H

Pharmacokinetics of Compound 72 in Rodents and Primates

Non-compartmental (model independent) methods were used to analyze the plasma concentration time-curves derived from all species as described below. Clearance (Cl), calculated percent extraction ratios (ER %), volume of distribution (Vz), time to ½-maximal concentration ($t_{1/2}$) and exposure (AUC, area under the curve) values are provided below for mouse, rat, and monkey, respectively.

1. Mouse: The pharmacokinetics of Compound 72 was examined following bolus intravenous (IV, 1 mg/kg) or oral (PO, 10 mg/kg) administration in female Balb/c mice (n=3/time point). Blood samples were obtained at 15 and 30 minutes, and 1, 2, 4, 8 and 24 hours after PO dosing, and at 15 and 30 minutes, and 1, 2, 4, and 8 hours for IV administration.

| IV: 1 mg/kg | Oral: 10 mg/kg |
|---|---|
| Cl = 2.6 · mL/min/kg | AUC = 10.5 µg-hr/kg |
| ER = 2.8% | F = 16% |
| $V_z$ = 0.085 L/kg | $C_{max}$ = 1.8 µg/mL |
| $t_{1/2}$ = 3.9 hrs | |
| AUC = 6.6 µg-hr/kg | |

2. Rat: The pharmacokinetics of Compound 72 was examined in male Sprague-Dawley rats (n=3/time point) following bolus IV (2 mg/kg) or PO (30 mg/kg) administration. Blood was sampled at the same time points as listed for the Mouse PK study.

| IV: 1 mg/kg | Oral: 30 mg/kg |
|---|---|
| Cl = 3.2 · mL/min/kg | AUC = 35 µg-hr/kg |
| ER = 4.6% | F = 15% |
| $V_z$ = 0.048 L/kg | $C_{max}$ = 4.5 µg/mL |
| $t_{1/2}$ = 3.9 hrs | |
| AUC = 4.7 µg-hr/kg | |

3. Monkey: The pharmacokinetics of Compound 72 was examined in male Cynomologus monkeys (n=3/time point) following bolus IV (2 mg/kg) or PO (10 mg/kg) administration. Blood was sampled at the same time points as listed for the Mouse PK study.

| IV: 1 mg/kg | Oral: 10 mg/kg |
|---|---|
| Cl = 8.8 · mL/min/kg | AUC = 7.6 µg-hr/kg |
| ER = 20% | F = 38% |
| $V_z$ = 3.2 L/kg | $C_{max}$ = 0.26 µg/mL |
| $t_{1/2}$ = 4.6 hrs | |
| AUC = 4.1 µg-hr/kg | |

Example I

Compound 72 in a Rat Model of Collagen Induced Arthritis (CIA)

Compound 72 was dosed in the prodrug form (Compound 74) in this study. Female Lewis rats (200 g); n=8 per treatment group were injected with type II collagen/Freund's incomplete adjuvant (300 µL injection of 0.6 mg collagen, dorsal surface Day 0 and Day 6). Animals were does with: (1) Vehicle: 5 mL/kg, PO, BID×7; (2) Compound 72: 0.3, 1, 3 or 10 mg/kg, PO, BID×7; or (3) ENBREL®: 10 mg/kg, SC, Days 1 and 4. ENBREL® served as a positive control. Compounds were administered on days 11-18. Ankle diameter was measured at day 11 and every day thereafter (FIG. 70). At study end paw weight and microscopic histology were determined. Both hind paws and knees were removed, hind paws weighed and then placed, with knees, in formalin. Following 1-2 days in fixative and 4-5 days in decalcifier, ankle joints and knees were processed, embedded, sectioned and stained with toluidine blue. Ankles and knees were given scores of 0-5 for inflammation, pannus formation and bone resorption.

The results show that Compound 72 dose-dependently improved all of the parameters associated with this disease model. For ankle diameter and histopathology, Compound 72 had an apparent $ED_{50}$ of 1.5 and 3.0 mg/kg, respectively. At 10 mg/kg Compound 72 induced disease regression by the end of the study.

Example J

Compound 72 Inhibits Angiogenesis In Vivo

Compound 72 was dosed in the prodrug form (Compound 74) in this study. Female CD-1 mice (19-22 g), n=4 per treatment group, were implanted subcutaneously with 500 µL growth factor reduced matrigel containing 1500 ng/mL bFGF or 0 ng/mL bFGF as a negative control. Test compounds were administered by oral gavage at the indicated doses and schedules. Animals were dosed with (1) Vehicle: 30 mM phosphate buffer, 10 mL/kg, PO, BID×7; (2) Compound 72: 10, 30 or 100 mg/kg active drug, PO, BID×7; or (3) SU11248: (Sutent) 40 mg/kg, PO, QD×7. Sutent is an inhibitor of KDRand served as a positive drug control in this study. Animals were euthanized on day 7. Matrigel was harvested, weighed and homogenized in phosphate buffered saline, pH 7.4. Samples were centrifuged and the resulting lysate analyzed for hemoglobin concentration by colorimetric reaction. Compound 72 inhibited bFGF-induced angiogenesis in a dose-dependent manner. At 100 mg/kg, angiogenesis was significantly inhibited by 72% (p<0.05, Dunnett's multiple comparison test).

Example K

Compound 72 Inhibits BCR-Abl-driven Tumors

Compound 72 was dosed in the prodrug form (Compound 74) in this study. Female Scid-beige mice (17-20 g), n=8 per group, were implanted with 107 K562 cells subcutaneously on the right flank. Test compounds were administered by oral gavage at the indicated doses and schedules when tumors reached 200±50 mm$^3$ in size. Animals were dosed with (1) Vehicle: 20% Trappsol, 10 mL/kg, PO, BID×7; (2) Compound 74: 30 or 100 mg/kg active drug, PO, BID or QD×7) or (3) Imatinib (GLEEVEC®): 400 mg/kg, PO, BID×7. Imatinib is a known inhibitor of Abl and served as a positive drug control in this study. Tumor size and body weight were monitored throughout the study. The results are shown in Table 6.

TABLE 6

| Treatment | % Regression and Complete responses |
| --- | --- |
| Imatinib | |
| 400 mg/kg BID | 98% R (6/8) |
| Compound 72 | |
| 30 mg/kg BID | Stasis (0/8) |
| 100 mg/kg BID | 93% R (5/8) |
| 100 mg/kg QD | Stasis (0/8) |

Compound 74 was efficacious in this model. Administration of 30 mg/kg BID or 100 mg/kg QD resulted in tumor stasis, and 94% tumor regression occurred and 5 or 8 animals had a complete response (100% tumor regression) when the dose was increased to 100 mg/kg BID. Compound 72 was well tolerated causing less than 10% body weight loss throughout the course of treatment.

Example L

Compound 72 in a Model of Multiple Myeloma

Compound 72 was dosed in the prodrug form (Compound 74) in this study. Female Scid-beige mice (17-20 g), n=8 per group, were implanted with 15×106 RPMI 8226 cells subcutaneously on the right flank with either vehicle (20% Trappsol, 10 mL/kg, PO, BID×14) or Compound 74 (100 mg/kg active drug, PO, BID×14). Test compounds were administered by oral gavage at the indicated doses and schedules when tumors reached 200±50 mm$^3$ in size. Tumor size and body weight were monitored throughout the study and Compound 72 was evaluated on the ability to inhibit tumor growth (% TGI=(1-T/C)×100). The results are shown in Table 7. Compound 72 (dosed in its pro-drug form as Compound 74) produced a statistically significant effect on tumor growth over the course of this study. These data suggest that the effect of Compound 72 observed in this study is in addition to or independent of its ability to inhibit p38. Compound 72 was well tolerated causing less than 10% body weight loss throughout treatment.

TABLE 7

| Group | % Tumor growth inhibition (TGI) |
| --- | --- |
| Control | 0% |
| Compound 37d 60 mg/kg | 31% |
| Compound 72 100 mg/kg | 67% |

The multiple myeloma cell line RPMI 8226 was treated with various concentrations of the proteasomal inhibitor MG-132 (to serve as a positive control) or Compound 72 for 72 hours at 37° C., 5% $CO_2$. Cell viability was then measured using CellTiter Blue (Promega) to determine $IC_{50}$ values for each compound (Table 8). Treatment with Compound 72 was not anti-proliferative over the indicated concentration range. MG-132 produced an $IC_{50}$ that was within historical ranges of in-house testing (Table 8). These data strongly indicate that the TGI effect observed for Compound 72 seen in vivo is likely due to extra-tumor effects. Such a role is consistent with published reports suggesting that the activity of both p38 and Tie2 may be critical for growth/survival of this type of tumor in vivo.

TABLE 8

| Compound | Proliferation $IC_{50}$ |
| --- | --- |
| MG-132 | 114 nM |
| Compound 72 | >10,000 nM |

Example M

Cell Activity of Compound 72 Against VEGFR2

HUVECs were serum-starved for 2 hours then treated with varying concentrations of Compound 72 or the control VEGFR2 inhibitor ((Z)-3-[(2,4-Dimethyl-3-(ethoxycarbonyl)pyrrol-5-yl)methylidenyl]indolin-2-one) for 60 minutes prior to stimulation with 20 ng/mL VEGF for 5 minutes. Lysates of the various treatments were prepared and immunoblotted with antibodies specific for VEGFR2 phosphorylated at Tyr1175. Resultant blots for Compound 72 and the control inhibitor VEGFR1 were then imaged and quantified using the LI-COR Aeriustm imager. Phospho-VEGFR2 signal was normalized to GAPDH as a loading control. These values were then used to generate $IC_{50}$ values for Compound 72 and the control VEGFR2 inhibitor VEGFR1, employing a 4-parameter curve fit protocol.

Compound 72 inhibits the vascular endothelial receptor type II (VEGFR2) autophosphorylation in HUVECs. The results show that Compound 72 treatment results in a dose-dependent inhibition of VEGFR2 autophosphorylation at Tyrosine residue 1175 with an $IC_{50}$ of 48 nM Preparative Examples In the examples described below, unless otherwise indicated, all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane (DCM), toluene, dioxane and 1,2-difluoroethane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

$^1$H-NMR spectra were recorded on a Varian instrument operating at 400 MHz. $^1$H-NMR spectra were obtained as CDCl$_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

Preparation of 1-(3-tert-butyl-1-p-tolyl-1H-pyrazol-5-yl)-3-(5-fluoro-2-(1-(2-hydroxyethyl)-1H-indazol-5-yloxy)benzyl)urea (72): Method 1

The synthesis of compound (72) according to Method 1 is shown in Scheme 1, steps A to J.

Step A: Preparation of 2-(benzyloxy)-5-fluorobenzonitrile 62: In a 12 L, 4-neck round bottom flask equipped with a mechanic stirrer and temperature probe, a suspension of sodium hydride (74 g, 1.82 mol) in DMF (1.95 L) was added benzyl alcohol (142 g, 1.3 mol) through a dropping funnel slowly over 30 minutes in an ice bath under nitrogen. The mixture was stirred in an ice bath (0° C.) for 120 minutes, a solution of 2,5-difluorobenzonitrile (180 g, 1.3 mol) in DMF (650 mL) was added through a dropping funnel over 35 minutes. The resulting mixture was warmed up to room temperature. After 2 hours, the mixture was cooled in an ice bath (4° C.) and quenched with saturated NH$_4$Cl (130 mL) followed by the addition of water (2.6 L×3). The slurry was stirred at room temperature overnight and the precipitate was filtered and washed with water (650 mL×3). The solid was dried in vacuum for 2 days to give 292 g (99.3%) of the desired compound. $^1$H NMR (400 MHz, DMSO-d$_6$) δ 7.78 (dd, 1H, J=3.2 Hz, J=8.2 Hz), 7.5-7.76 (m, 1H), 7.35-7.48 (m, 6H), 5.28 (s, 2H).

Step B: Preparation of 5-Fluoro-2-hydroxybenzonitrile 63: Dry 10% Pd/C (2.48 g) was placed in a 5 L flask under N$_2$. A solution of 2-(benzyloxy)-5-fluorobenzonitrile (148 g, 651 mmol) in methanol (2.34 L) was added slowly under N$_2$. The air of the flask was removed by vacuum and the flask was charged with H$_2$ (balloon) three times. The mixture was stirred at room temperature for 1 hour. The above process was repeated two more times to push the reaction to completion. The mixture was stirred at room temperature for another 2 hours. The mixture was filtered through a Celite pad under N$_2$ and washed with EtOAc (150 mL×2). The palladium waste was rinsed with water (50 mL) and discarded. The filtrates were concentrated to give (94.6 g, 106%) of the desired compound as a yellow solid. MS (APCI-) m/z 137 (M-1) was detected. $^1$H NMR (400 MHz, DMSO-d$_6$) δ 11.07 (br, 1H), 7.58 (dd, 1H, J=3.2 Hz, J=8.2 Hz), 7.43 (m, 1H), 6.91-7.03 (dd, 1H J=4.5 Hz, J=9.2 Hz).

Step C: Preparation of 5-Fluoro-2-(4-methyl-3-nitrophenoxy) benzonitrile 64: In a 3-necked 5 L flask, equipped with a mechanic stirrer, a condenser, and a J-Kem temperature probe, a solution of 5-fluoro-2-nitrotoluene (158 g, 1.02 mol) in N,N-dimethylacetamide (500 mL) was added to a mixture of 5-fluoro-2-hydroxybenzonitrile (147 g, 1.07 mol) and potassium carbonate (163 g, 1.2 mol) in N,N-dimethylacetamide (573 mL) at room temperature. The mixture was heated to 100° C. After 8 hours, the reaction mixture was cooled to room temperature and water (3400 mL) was added in an ice bath. The precipitate was filtered, washed with water (1073 mL×2), and dried in vacuum (40° C.) to give (264 g, 90%) of the desired compound as a brown solid. MS (APCI-) m/z 272 (M-1) was detected. $^1$H NMR (400 MHz, CDCl$_3$) δ 8.10 (d, 1H, J=9 Hz), 7.41-7.48 (m, 1H), 7.38 (m, 1H), 7.07-7.14 (m, 1H), 6.88-7.10 (m, 1H), 2.63 (s, 3H).

Step D: Preparation of 2-(3-Amino-4-methylphenoxy)-5-benzonitrile 65: In a 4-neck 12000 mL round bottom flask, equipped with a mechanic stirrer, a condenser, and a J-Kem temperature probe, 2-(3-amino-4-methylphenoxy)-5-benzonitrile (247 g, 907 mmol) and Zn dust (297 g, 4.5 mol) were placed and suspended in 1:1 MeHH/THF (2.2 L). Saturated aqueous NH$_4$Cl (1.6 L) was added slowly over 40 minutes through an addition funnel (maintaining the internal temperature below 60° C.). The reaction mixture was cooled to room temperature and stirred at room temperature for 1 hour. Zinc dust was removed by filtration and the cake was washed with EtOAc (450 mL×3). Saturated aqueous NH$_4$OAc (1500 mL, prepared from 2 kg of NH$_4$OAc and 4 L of H$_2$O) and H$_2$O (1500 mL×2) were added. The filtrates were concentrated by rotary evaporation until mostly water remained. The tan solid was filtered and washed with H$_2$O (1500 mL×4), and dried in vacuum to provide 211.5 g (96%) of the desired compound. MS (APCI+) m/z 243 (M+1) was detected. $^1$H NMR (400 MHz, CDCl$_3$) δ 7.38 (m, 1H), 7.18 (m, 1H), 6.65-6.85 (m, 5H), 3.60 (br, 2H), 2.17 (s, 3H).

Step E: Preparation of 2-(1H-indazol-5-yloxy)-5-fluorobenzonitrile 66: In a 6 L round bottom flask equipped with a mechanic stirrer, J-KEM temperature probe, a cold solution (0° C.) of 2-(3-amino-4-methylphenoxy)-5-benzonitrile (209 g, 862 mmol) and NH$_4$BF$_4$ in acetic acid (1.75 L)/water (862 mL) was treated with concentrated HCl (359 mL) dropwise over 2 minutes. The slurry was stirred in an ice bath for 30 minutes and sodium nitrite was added. The reaction mixture was stirred at 0° C. for 1 hour and then warmed to room temperature. After stirring at room temperature for 3 hours, solvents were removed by rotary evaporation and azeotroped with toluene (200 mL×2). The residue was dried in vacuum overnight. The solid was suspended in acetone (200 mL) and EtOAc (200 mL) and the solvents were removed by rotary evaporation. The residue was suspended in EtOAc (200 mL) and removed by rotary evaporation. The residue was suspended in EtOAc (1145 mL) and potassium acetate (254 g, 2.6 mol) was added in one portion. The mixture was stirred at room temperature for 20 hours and filtered. The cake was washed with EtOAc (500 mL×6). The combined filtrates were concentrated. The residue was suspended in EtOAc (500 mL) and heptane (500 mL). The yellow solid was filtered (141.3 g). The mother liquor was concentrated and recrystallized from MTBE/Hexane (100 mL/100 mL) to afford 20.1 g. The second mother liquor was concentrated and triturated with MTBE/heptane (100 mL/100 mL) to give an additional 14.28 g. Combined crops yielded 176 g (81% yield) of the desired compound. MS (APCI+) m/z 254 (M+1) detected. $^1$H NMR (400 MHz, DMSO-d$_6$) δ 13.38 (br, 1H), 8.07 (s, 1H), 7.94 (dd, 1H, J=3,1 Hz, J=8.2 Hz), 7.64 (d, 1H, J=9 Hz), 7.54 (m, 2H), 7.21 (dd, 1H, J=9 Hz), 6.96 (dd, 1H, J=4.3 Hz, J=9.3 Hz).

Step F: Preparation of 2-(1-(2,2-dimethoxyethyl)-1H-indazol-5-yloxy)-5-fluorobenzonitrile 67: 2-(1H-Indazol-5-yloxy)-5-fluorobenzonitrile (5.000 g, 19.7 mmol) was suspended in N,N-dimethylacetamide (50 mL) and sodium hydride (0.684 g, 25.7 mmol) was added portionwise at room temperature. 2-Bromo-1,1-dimethoxyethane (3.49 mL, 29.6 mmol) was added dropwise in one portion and the reaction mixture was heated to 80° C. for 18 hours. The reaction mixture was cooled to room temperature and concentrated under reduced pressure to afford the crude material, which was partitioned between EtOAc and saturated aqueous NH$_4$Cl. The combined organic layers were washed with water (3×), brine and dried (MgSO$_4$) and then concentrated under reduced pressure to afford the crude material. The crude product was purified by flash column chromatography (eluant 25% EtOAc/Hexanes) to furnish 3.88 g (57.6%) of the desired compound. The N-2 isomer was not isolated. MS (APCI+) m/z 342 (M+1) was detected. $^1$H NMR (400 MHz, CDCl$_3$) δ 7.98 (s, 1H), 7.54 (d, 1H, J=9 Hz), 7.36 (m, 2H), 7.16 (m, 2H), 6.82 (dd, 1H, J=4.3 Hz, J=9.3 Hz), 4.76 (t, 1H, J=5.3 Hz), 4.49 (d, 2H, J=5.3 Hz), 3.41 (s, 6H).

Step G: Preparation of (2-(1-(2,2-dimethoxyethyl)-1H-indazol-5-yloxy)-5-fluorophenyl)methanamine 68: 2-(1-(2,2-Dimethoxyethyl)-1H-indazol-5-yloxy)-5-fluorobenzonitrile (3.80 g, 11.13 mmol) in THF (100 mL) was added dropwise to a stirred 0° C. suspension of lithium aluminum hydride (0.6338 g, 16.70 mmol) in THF (100 mL). The reaction mixture was maintained at 0° C. until complete addition of the starting material was achieved. The reaction mixture was warmed to room temperature and stirred until complete consumption of starting material was seen by HPLC analysis. The reaction mixture was added dropwise to a stirred room temperature solution of saturated aqueous Rochelle's salt. The two phase mixture was rapidly stirred for 30 minutes until the aluminum salts were in solution. The layers were separated and the aqueous layer extracted with more EtOAc. The combined organics were dried (MgSO$_4$) and concentrated under reduced pressure to afford 3.73 g (97%) of the crude product, which was used without further purification. MS (APCI+) m/z 346 (M+1) was detected. $^1$H NMR (400 MHz, CDCl$_3$) δ 7.90 (s, 1H), 7.48 (d, 1H, J=9 Hz), 6.9-7.15 (m, 5H), 4.76 (t, 1H, J=5.3 Hz), 4.49 (d, 2H, J=5.3 Hz), 3.88 (s, 2H), 3.36 (s, 6H).

Step H: Preparation of 1-(3-tert-butyl-1-p-tolyl-1H-pyrazol-5-yl)-3-(241-(2,2-dimethoxyethyl)-1H-indazol-5-yloxy)-5-fluorobenzyl)urea 70: (2-(1-(2,2-dimethoxyethyl)-1H-indazol-5-yloxy)-5-fluorophenyl)methanamine (2.00 g, 5.791 mmol), 2,2,2-trichloroethyl 3-tert-butyl-1-p-tolyl-1H-pyrazol-5-ylcarbamate (3.516 g, 8.686 mmol) and N,N-diisopropylethylamine (3.026 mL, 17.37 mmol) were suspended in N,N-dimethylacetamide (50 mL) and heated at 80° C. overnight. The reaction mixture was concentrated under reduced pressure and the residue diluted with EtOAc and saturated aqueous NH$_4$Cl. The organics were washed with water (3×), brine, dried (MgSO$_4$) and then concentrated under reduced pressure to afford the crude material, which was purified by flash column chromatography (eluant 35-45% EtOAc/Hexanes). After evaporation of the solvent, the desired product was obtained as a pale yellow foam (2.57 g, 74%). MS (APCI+) m/z 602 (M+1) was detected. $^1$H NMR (400 MHz, DMSO-d$_6$) δ 7.88 (s, 1H), 7.43 (d, 1H, J=9 Hz), 6.72-7.30 (m, 9H), 6.18 (s, 1H), 6.01 (br, 1H), 5.47 (t, 1H, J=6.1 Hz), 4.76 (t, 1H, J=5.3 Hz), 4.44 (t, 4H, J=5.6 Hz), 3.38 (s, 6H), 2.37 (s, 3H), 1.30 (s, 9H).

Step I: Preparation of 1-(3-tert-butyl-1-p-tolyl-1H-pyrazol-5-yl)-3-(5-fluoro-2-(1-(2-oxoethyl)-1H-indazol-5-yloxy)benzyl)urea 71: 1-(3-tert-Butyl-1-p-tolyl-1H-pyrazol-5-yl)-3-((2-(1-(2,2-dimethoxyethyl)-1H-indazol-5-yloxy)-5-fluorophenyl)methyl)urea (0.500 g, 0.8324 mmol) dissolved in dichloromethane at room temperature and iodotrimethylsilane (0.3554 mL, 2.497 mmol) added dropwise to the stirred solution. The reaction mixture was monitored by HPLC analysis and when no starting material was detected, the mixture was diluted with dichloromethane and washed with 10% aqueous Na$_2$S$_2$O$_4$, saturated aqueous NaHCO$_3$, brine, dried (MgSO$_4$) and concentrated under reduced pressure to afford 536 mg (quant. yield) of the crude product, which was used without further purification. $^1$H NMR (400 MHz, DMSO-d$_6$) δ 9.76 (s, 1H), 7.97 (s, 1H), 6.78-7.30 (m, 10H), 6.17 (s, 1H), 5.99 (br, 1H), 5.44 (q, 1H, J=6.1 Hz), 4.46 (m, 4H), H 2.35 (s, 3H), 1.34 (s, 9H).

Step J: Preparation of 1-(3-tert-butyl-1-p-tolyl-1H-pyrazol-5-yl)-3-(5-fluoro-241-(2-hydroxyethyl)-1H-indazol-5-yloxy)benzyl)urea 72: 1-(3-tert-Butyl-1-p-tolyl-1H-pyrazol-5-yl)-3-((5-fluoro-2-(1-(2-oxoethyl)-1H-indazol-5-yloxy)phenyl)methyl)urea (2.179 g, 3.929 mmol) was suspended in MeOH (40 mL) and treated with sodium borohydride (0.7432 g, 19.64 mmol) portionwise at room temperature. The reaction mixture was stirred at room temperature until complete conversion of the starting material to product was observed by HPLC analysis. The reaction mixture was concentrated under reduced pressure and then diluted with saturated aqueous NH$_4$Cl and extracted into dichloromethane. The organics were dried (MgSO$_4$) and concentrated under reduced pressure to afford the crude material, which was purified by flash column chromatography (eluant 2-6% iPrOH/DCM) to provide 1.21 g (55%) of the desired compound. MS (APCI+) m/z 557 (M+1) was detected. $^1$H NMR (400 MHz, DMSO-d$_6$) δ 8.29 (s, 1H), 7.97 (s, 1H), 7.68 (d, 1H, J=9.1 Hz), 7.35 (s, 1H), 6.85-7.4 (m, 8H), 6.24 (s, 1H), 4.87 (t, 1H, J=5.4 Hz), 4.43 (t, 1H, J=5.6 Hz), 4.28 (d, 1H, J=5.9 Hz), 3.80 (q, 1H, J=5.5 Hz), 2.35 (s, 3H), 1.25 (s, 9H).

Example 2

Preparation of 2-(5-(2-(3-(3-tert-butyl-1-p-tolyl-1H-pyrazol-5-yl)ureido)methyl)-4-fluorophenoxy)-1H-indazol-1-yl)ethyl dihydrogenphosphate (74):
Method 1

The synthesis of compound (74) according to Method 1 is shown in Scheme 1, steps K to L.

Step K: Preparation of dibenzyl 245-(243-(3-tert-butyl-1-p-tolyl-1H-pyrazol-5-yl)ureido)methyl)-4-fluorophenoxy)-1H-indazol-5-yl)ethylphosphate 73: 1-(3-tert-Butyl-1-p-tolyl-1H-pyrazol-5-yl)-3-((5-fluoro-2-(1-(2-hydroxyethyl)-1H-indazol-5-yloxy)phenyl)methyl)urea (0.357 g, 0.6414 mmol), diphenyl diisopropylphosphoramidite (0.2970 ml, 0.9620 mmol) and 2H-tetrazole (0.07189 g, 1.026 mmol) were suspended in DMF (10 mL) and stirred at room temperature until TLC (10:1 DCM-Et$_2$O) analysis showed complete consumption of starting material. t-Butyl hydrogen peroxide (0.4439 mL, 3.207 mmol) was added and then the reaction monitored by HPLC analysis. Upon completion of the reaction, 10% aqueous Na$_2$S$_2$O$_3$ was added and the reaction mixture was stirred for 10 minutes. The reaction mixture was poured into saturated aqueous NaHCO$_3$ and extracted into EtOAc. The combined organics were washed with water (2×) and brine. The organics were dried (MgSO$_4$) and concentrated under reduced pressure to afford the crude material, which was purified by flash column chromatography (eluant 30-40% EtOAc/Hexanes) to provide 458 mg (87%) of the desired compound. MS (APCI+) m/z 817 (M+1) was detected. $^1$H NMR (400 MHz, CDCl$_3$) δ 7.85 (s, 1H), 6.7-7.35 (m, 10H), 6.18 (s, 1H), 6.16 (s, 1H), 4.62 (s, 1H), 5.36 (t, 1H, J=6 Hz), 4.81 (d, 4H, J=8.2 Hz), 4.54 (t, 2H, J=5.1 Hz), 4.39 (m, 4H), 2.35 (s, 3H), 1.25 (s, 9H).

Step L: Preparation of 2-(5-(2-((3-(3-tert-butyl-1-p-tolyl-1H-pyrazol-5-yl)ureido)methyl)-4-fluorophenoxy)-1H-indazol-1-yl)ethyl dihydrogenphosphate 74: Dibenzyl 2-(5-(2-((3-(3-tert-butyl-1-p-tolyl-1H-pyrazol-5-yl)ureido)methyl)-4-fluorophenoxy)-1H-indazol-1-yl)ethyl phosphate (1.920 g, 2.35 mmol) was suspended in EtOH (0.05M, 50 mL) and cyclohexa-1,4-diene (3.56 ml, 82.14 mmol) and 10% Pd/C (20%/weight, 0.384 g) were added. The reaction mixture was refluxed overnight. The reaction mixture was filtered through GF paper and washed with MeOH. The organic layers were concentrated under reduced pressure to afford the crude material, which was dissolved in MeOH and passed through a Gellman acrodisk (0.45 um) filter to remove trace of palladium contamination. After evaporation of the solvent, the resulting gum was triturated in $CH_3CN$ and solids formed were collected by filtration and dried under high vacuum for 3 hours to provide 1.21 g (89%) of the desired compound. MS (APCI+) m/z 637 (M+1) was detected. $^1$H NMR (400 MHz, DMSO-$d_6$) δ 8.30 (s, 1H), 8.00 (s, 1H), 7.71 (d, 1H, J=9 Hz), 6.88-7.37 (m, 10H), 6.24 (s, 1H), 4.61 (br, 1H), 4.28 (d, 2H, J=5.7 Hz), 4.19 (dd, 2H, J=5.2 Hz), 2.35 (s, 3H), 1.25 (s, 9H).

Example 3

Preparation of 1-(3-tert-Butyl-1-p-tolyl-1H-pyrazol-5-yl)-3-((5-fluoro-2-(1-(2-hydroxyethyl)-1H-indazol-5-yloxy)phenyl)methyl)urea (72): Method 2

An alternative method for the synthesis of compound (72), according to Method 2, is shown in Scheme 2, steps A to F.

Step A: Preparation of 2-(4-amino-3-methylphenoxy)-5-fluorobenzonitrile 65: In a 3 L, 4-necked flask that had been evacuated and back-filled with argon, 2,5-difluorobenzonitrile (295.3 ml, 812.0 mmol) and 4-amino-3-methylphenol (100.0 g, 812.0 mmol) were dissolved in dry DMSO (2.75 M) with rapid stirring at room temperature. The solution was evacuated/backfilled with argon (3×). Potassium carbonate (185.2 g, 1340 mmol) (−325 mesh) was added. The reaction mixture was evacuated/backfilled with argon (3×) and warmed to 80° C. (internal probe) for 16 hours. TLC indicated complete conversion. The reaction mixture was cooled to room temperature and poured slowly into 2 L of ice water with rapid stirring. The residue in the round bottom flask was taken up in water repeatedly and poured into the ice water until a total volume of 3 L was achieved and all solids were in the ice water. The suspension was stirred rapidly for 2 hours as it came to room temperature. The brown solids were collected by filtration, washed with water (3 L), air dried, dried with latex dam, and dried under high vacuum at 40° C. for 44 hours to provide 194 g (99%) of the desired product as a tan solid. MS (APCI+) m/z 243 (M+1) was detected. $^1$H NMR (400 MHz, $CDCl_3$) δ 7.38 (m, 1H), 7.18 (m, 1H), 6.65-6.85 (m, 5H), 3.60 (br, 2H), 2.17 (s, 3H).

Step B: Preparation of 2-(1H-Indazol-5-yloxy)-5-fluorobenzonitrile 66: In a 500 mL one-necked flask containing a large magnetic stir bar, 2-(4-amino-3-methylphenoxy)-5-fluorobenzonitrile (274.5 ml, 219.6 mmol) was taken up in chloroform (0.8 M) and treated with potassium acetate (25.86 g, 263.5 mmol) at room temperature. The reaction mixture was cooled to 0° C. and treated with acetic anhydride (62.28 mL, 658.8 mmol) via addition funnel over 5 minutes. The reaction was fitted with a reflux condenser, treated with additional 100 mL chloroform, and heated to 40° C. Isoamyl nitrite (58.74 mL, 439.2 mmol) was added dropwise via an addition funnel. The addition funnel was rinsed with 60 mL+40 mL of chloroform, removed, and replaced with a glass stopper. The reaction was heated to reflux for 20 hours, cooled to room temperature, and concentrated in vacuo to a brown solid. After being dried under high vacuum for 30 minutes, the brown solid was suspended in 1 L water, stirred vigorously for 15 minutes, and filtered. The resulting orange-brown solid (83 g) was taken up in 400 mL MeOH and treated with 1.0 M hydrochloric acid (241.6 mL, 241.6 mmol) at room temperature. The mixture was fitted with a reflux condenser and warmed to 70° C. for 20 hours. The reaction was cooled to 0° C. and 1.0 M sodium hydroxide (252.6 mL, 252.6 mmol) was added, followed by water (250 mL). The resulting yellow suspension was stirred in the ice bath for 10 minutes and then allowed to settle. The suspension was filtered, washed with water (1 L), air dried, dried with latex dam, and dried under high vacuum at 40° C. for 36 hours, to provide 50.7 g (91%) of the desired product as a free-flowing tan solid. MS (APCI+) m/z 254 (M+1) detected. $^1$H NMR (400 MHz, DMSO-$d_6$) δ 13.38 (br, 1H), 8.07 (s, 1H), 7.94 (dd, 1H, J=3,1 Hz, J=8.2 Hz), 7.64 (d, 1H, J=9 Hz), 7.54 (m, 2H), 7.21 (dd, 1H, J=9 Hz), 6.96 (dd, 1H, J=4.3 Hz, J=9.3 Hz).

Step C: Preparation of methyl 2-(5-(2-cyano-4-fluorophenoxy)-1H-indazol-1-yl)acetate 77: 2-(1H-Indazol-5-yloxy)-5-fluorobenzonitrile (40.7 g, 160.7 mmol) was dissolved in 400 mL of DMF and the solution was placed in a water bath (room temperature). Cesium carbonate (157.1 g, 482.2 mmol) was added. After 30 minutes in a water bath, methyl 2-bromoacetate (33.47 ml, 353.6 mmol) was added dropwise. The mixture was stirred at room temperature for 4 hours. To the mixture was added water (400 mL, slightly exothermic) and the whole mixture was transferred to a 2 L separatory funnel (contained 400 mL of EtOAc). Layers were separated, and the aqueous layer was extracted with EtOAc (3×200 mL). The combined extracts were washed with water and brine and the layers were separated. The organic layer was dried over $MgSO_4$, filtered through a Celite pad, concentrated under reduced pressure, and dried under high vacuum for 1 hour to provide 66.3 g of tan solid. The solid was dissolved in 400 mL of hot EtOAc and treated with charcoal for 10 minutes under reflux. The mixture was filtered through a Celite pad and concentrated under reduced pressure. Insoluble materials were removed by filtration. The solid was dissolved in 300 mL of hot EtOAc and 300 mL of hexanes were added. The mixture was cooled to room temperature. Light brown solid was collected by filtration, 32.24 g (61.7%). MS (APCI+) m/z 326 (M+1) was detected. $^1$H NMR (400 MHz, $CDCl_3$) δ 8.03, 1H), 7.41-7.36 (m, 3H), 7.22-7.16 (m, 2H), 6.81 (dd, J=4.29 Hz, 9.37 Hz, 1H), 5.19 (s, 2H), 3.79 (s, 3H).

Step D: Preparation of methyl 2-(5-(2-(aminomethyl)-4-fluorophenoxy)-1H-indazol-1-yl)acetate dihydrochloride 78: Methyl 2-(5-(2-cyano-4-fluorophenoxy)-1H-indazol-1-yl)acetate (10.00 g, 30.74 mmol) was placed in a 2500 mL Parr hydrogenation vessel. Methanol (0.1M, 310 mL) and concentrated HCl (25.62 ml, 307.4 mmol) were added. 10% Pd/C (2.0 g, Degussa type) was added and the vessel was purged with hydrogen gas (three times, no vacuum evacuation was done). The vessel was charged with hydrogen gas at 40 psi and was left on the shaker for 18 hours. To the mixture was added additional 1.0 g of 10% Pd/C and the mixture was placed back in the Parr hydrogenator for an additional 18 hours. The mixture was filtered through a Celite pad and concentrated under reduced pressure (bath temperature kept below 20° C.). The residue was azeotroped with MeOH (3×100 mL). The bath temperature was raised to 40° C. after the third azeotrope. The residue (oil) was dried under high vacuum for 2 hours to provide the desired product as a yellow solid (11.6 g, 93.8%). MS (APCI+) m/z 330 (M+1) was detected. $^1$H NMR (400 MHz, DMSO-d$_6$) δ 8.08 (s, 1H), 6.84-7.76 (m, 6H), 5.43 (s, 2H), 4.8 (br, 2H), 4.105 (q, 2H, J=5.6 Hz), 3.68 (s, 3H).

Step E: Preparation of Methyl 2-(5-(2-((3-(3-tert-butyl-1-p-tolyl-1H-pyrazol-5-yl)ureido)methyl)-4-fluorophenoxy)-1H-indazol-1-yl)acetate 79: A solution of methyl 2-(5-(2-(aminomethyl)-4-fluorophenoxy)-1H-indazol-1-yl)acetate dihydrochloride (17.5 g, 43.51 mmol) in dimethylacetamide (0.5M, 88 mL) was treated with 2,2,2-trichloroethyl-3-tert-butyl-1-p-tolyl-1H-pyrazol-5-ylcarbamate (17.96 g, 44.38 mmol), followed by diisopropylethylamine (30.3 mL, 174 mmol) at room temperature. The mixture was heated at 80° C. overnight. The mixture was concentrated in vacuo and the residue distributed between EtOAc and saturated aqueous NH$_4$Cl. The organic layer was separated and washed with brine, filtered through 1PS paper, evaporated in vacuo to a brown foam. The foam was triturated in ether, and the precipitated solids were collected by filtration to provide 22.55 g (89%) of the desired compound. MS (APCI+) m/z 585 (M+1) detected. $^1$H NMR (400 MHz, DMSO-d$_6$) δ 8.3 (s, 1H), 8.07 (s, 1H), 7.68 (d, 1H, J=8.9 Hz), 6.85-7.37 (m, 8H), 6.24 (s, 1H), 5.4 (s, 2H), 4.28 (d, 2H, J=5.8 Hz), 3.68 (s, 3H), 2.35 (s, 3H), 1.25 (s, 9H).

Step F: Preparation of 1-(3-tert-Butyl-1-p-tolyl-1H-pyrazol-5-yl)-3-((5-fluoro-2-(1-(2-hydroxyethyl)-1H-indazol-5-yloxy)phenyl)methyl)urea 72: A solution of methyl 2-(5-(2-((3-(3-tert-butyl-1-p-tolyl-1H-pyrazol-5-yl)ureido)methyl)-4-fluorophenoxy)-1H-indazol-1-yl)acetate (4.6 g, 7.87 mmol) in methanol (0.1M, 80 mL) was treated with sodium borohydride (893 mg, 23.6 mmol) in portions at room temperature. The mixture was stirred at room temperature for 18 hours, and the solvent evaporated in vacuo to a dark yellow residue. The residue was distributed between dichloromethane and saturated aqueous NH$_4$Cl. The organic layer was filtered through 1PS paper, evaporated in vacuo and purified in Biotage eluting with 2-10% iPrOH/DCM. Desired fractions were evaporated in vacuo to a white foam, 2.97 g (68%). MS (APCI+) m/z 557 (M+1) was detected. $^1$H NMR (400 MHz, DMSO-d$_6$) δ 8.29 (s, 1H), 7.97 (s, 1H), 7.68 (d, 1H, J=9.1 Hz), 7.35 (s, 1H), 6.85-7.4 (m, 8H), 6.24 (s, 1H), 4.87 (t, 1H, J=5.4 Hz), 4.43 (t, 1H, J=5.6 Hz), 4.28 (d, 1H, J=5.9 Hz), 3.80 (q, 1H, J=5.5 Hz), 2.35 (s, 3H), 1.25 (s, 9H).

Example 4

Preparation of 2-(5-(2-((3-(3-tert-butyl-1-p-tolyl-1H-pyrazol-5-yl)ureido)methyl)-4-fluorophenoxy)-1H-indazol-1-yl)ethyl dihydrogenphosphate (74): Method 2

An alternative method for the synthesis of compound (72), according to Method 2, is shown in Scheme 2, steps G to H.

Step G: Preparation of di-tert-butyl 2-(5-(2-((3-(3-tert-butyl-1-p-tolyl-1H-pyrazol-5-yl)ureido)methyl)-4-fluorophenoxy)-1H-indazol-1-yl)ethyl phosphate 80: A solution of 1-(3-tert-butyl-1-p-tolyl-1H-pyrazol-5-yl)-3-((5-fluoro-2-(1-(2-hydroxyethyl)-1H-indazol-5-yloxy)phenyl)methyl)urea (1.5 g, 2.69 mmol) in DMF (0.2M, 15 mL) was treated with imidazole (183 mg, 2.69 mmol), and imidazole hydrochloride (423 mg, 4.04 mmol) at room temperature. After complete dissolution was observed, di-tert-butyl diisopropylphosphoramidite (1.28 mL, 4.04 mmol) was added. Stirring was continued at room temperature for 18 hours. Hydrogen peroxide (50% aqueous, 0.535 mL, 9.43 mmol) was added at room temperature slowly, and stirring was continued for 1 hour. The reaction was completed as detected by LC and TLC. The residue was distributed between dichloromethane and 10% aqueous Na$_2$S$_2$O$_3$. The aqueous layer was extracted with EtOAc (2×). The combined organic extracts were washed with brine, filtered through 1PS paper, evaporated in vacuo to yellow oil. The oil was purified by a silica gel plug eluting with DCM, 3-5% MeOH/DCM. Desired fractions were evaporated in vacuo to provide the desired product as a white foam, 1.59 g (79%). MS (APCI+) m/z 749 (M+) was detected. $^1$H NMR (400 MHz, DMSO-d$_6$) δ 8.29 (s, 1H), 8.01 (s, 1H), 7.73 (d, 1H, J=9.1 Hz), 6.79-7.35 (m, 8H), 6.23 (s, 1H), 4.62 (t, 2H, J=4.7 Hz), 4.26 (m, 4H), 2.35 (s, 3H), 1.43, s, 9H), 1.25 (s, 18H).

Step H: Preparation of 2-(5-(243-(3-tent-butyl-1-p-tolyl-1H-pyrazol-5-yl)ureido)methyl)-4-fluorophenoxy)-1H-indazol-1-yl)ethyl dihydrogenphosphate 74: A solution of di-tert-butyl 2-(5-(2-((3-(3-tert-butyl-1-p-tolyl-1H-pyrazol-5-yl)ureido)methyl)-4-fluorophenoxy)-1H-indazol-1-yl)ethyl phosphate (3.66 g, 4.89 mmol) in EtOH (0.2M, 24 mL) was treated with 5N HCl/iPrOH (2.93 mL, 14.7 mmol) at room temperature. Stirring at room temperature was continued overnight. The solvent was evaporated in vacuo, and the residue was coevaporated from toluene, and ether (2×). The beige foam was taken in MeOH and poured slowly into a beaker containing water. The precipitated solids were collected by filtration to provide 2.83 g (91%) of the desired product. MS (APCI+) m/z 637 (M+1) was detected. $^1$H NMR (400 MHz, DMSO-d$_6$) δ 8.30 (s, 1H), 8.00 (s, 1H), 7.71 (d, 1H, J=9 Hz), 6.88-7.37 (m, 10H), 6.24 (s, 1H), 4.61 (br, 1H), 4.28 (d, 2H, J=5.7 Hz), 4.19 (dd, 2H, J=5.2 Hz), 2.35 (s, 3H), 1.25 (s, 9H).

Example 5

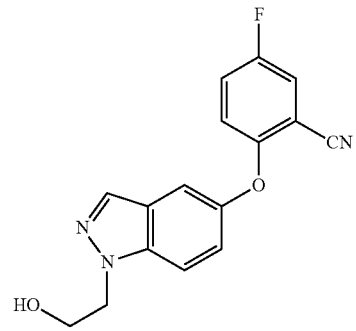

5-fluoro-2-(1-(2-hydroxyethyl)-1H-indazol-5-yloxy) benzonitrile (78A)

To a solution of methyl 2-(5-(2-cyano-4-fluorophenoxy)-1H-indazol-1-yl)acetate 77 (prepared as in Example 3) (60.0 g, 184.4 mmol) in MeOH (370 mL) was added NaBH$_4$ (24.42 g) in five 5 gram portions over 90 minutes. The temperature rose from 25° C. to 44.7° C. at the final addition of NaBH$_4$. The mixture was concentrated under vacuum. To the concentrate was added saturated NH$_4$Cl (600 mL) and EtOAc (600 mL) and the mixture was vigorously stirred for 1 hour. The layers were separated and the aqueous layer was extracted with EtOAc (2×100 mL). The combined organics were washed with saturated NH$_4$Cl (2×100 mL), water (200 mL), brine (500 mL), dried over MgSO$_4$, filtered thru GF/F paper and concentrated to a bright orange solid. The crude solid was dissolved in CH$_2$Cl$_2$ (1 L) and hexanes (2.25 L) were added with stirring. A light brown solid formed and after stirring for 30 min the solid was collected and dried under high vacuum to yield 45.5 g. The filtrate was concentrated under reduced pressure. This material was redissolved in $CH_2Cl_2$ (100 mL) and hexanes were added (200 mL). The resulting solid (6.2 g) was collected via filtration. The two crops were combined to give 51.7 g (94.3%) of 78A. $^1$H NMR (400 MHz, $CDCl_3$) δ 7.99 (s, 1H), 7.49 (d, 1H), 7.39-7.36 (m, 2H), 7.21-7.16 (m, 2H), 6.90 (dd, 1H), 4.49 (t, 2H), 4.17-4.13 (m, 2H), 2.81 (t, 1H).

Example 6

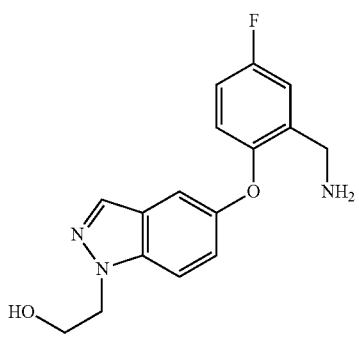

2-(5-(2-(aminomethyl)-4-fluorophenoxy)-1H-indazol-1-yl)ethanol (79A) Method A

To a 250 mL Parr shaker was added 5-fluoro-2-(1-(2-hydroxyethyl)-1H-indazol-5-yloxy)benzonitrile 78A (prepared as in Example 5) (80.0 g, 269.1 mmol), $Pd(OH)_2$ (32 g, 40% loading), EtOH (5 L) and concentrated HCl (224 mL, 2691 mmol). The vessel was sealed, purged with hydrogen, vented and charged with hydrogen to 180 PSI. The internal temperature was lowered to 18° C. and after stirring for 23 hours the reaction was judged complete by HPLC. The above reaction mixture was removed and the entire sequence was repeated twice with 80 g of starting material, and then with 53.2 g of starting material. The combined reaction mixtures (4 reactions) were filtered thru GF/F and the filtrate was concentrated under reduced pressure. The residue was dissolved in 1 N HCl (3.0 L) and washed with EtOAc (3×2 L). To the aqueous layer was added EtOAc (2 L) and the phases were vigorously stirred for 10 minutes and then the organic layer was removed. This step was repeated 2 more times and the aqueous layer was transferred to a cooled flask (ice bath). To the acidic aqueous mixture was added NaOH pellets (40 g×11) in a manner such that the temperature did not rise above 35° C. Once the pH was ~14 the mixture was transferred to a separatory funnel and extracted with $CH_2Cl_2$ (4×1 L). The combined extracts were washed with water (2×1 L) and brine (2×1 L). The extract was dried over $MgSO_4$ (~250 g), filtered thru GF/F and concentrated under reduced pressure. The concentrate was dissolved in $CH_2Cl_2$ (3.5 L) and hexanes were added (4 L). After the first 2 L of hexanes were added a brown solid formed. After stirring for 1 hour the solid was collected via filtration and the cake was washed with 1:2 $CH_2Cl_2$/hexanes (500 mL). The cake was dried under vacuum to yield 165.1 g (55.6%) of 79A. $^1$H NMR (400 MHz, $CDCl_3$) δ 7.90 (s, 1H), 7.42 (d, 1H), 7.17-7.12 (m, 3H), 6.87 (td, 1H), 6.80 (dd, 1H), 4.46 (t, 2H), 4.12 (t, 2H), 3.86 s (2H), 1.87 (br s, 1H).

Example 7

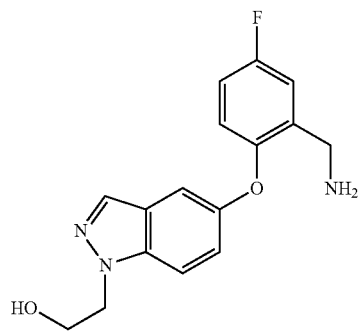

2-(5-(2-(Aminomethyl)-4-fluorophenoxy)-1H-indazol-1-yl)ethanol (79A) (Method B)

To a solution of (5-fluoro-2-(1-(2-hydroxyethyl)-1H-indazol-5-yloxy)benzonitrile (1.0 g, 3.36 mmol) and $NiCl_2 6H_2O$ (148 mg, 0.336 mmol) in MeOH (30 mL) was added $NaBH_4$ (636 mg, 16.8 mmol) in portions (2-3), and the reaction was stirred for 3 hours. A solution of saturated $Na_2CO_3$ (15 mL) was slowly added and the mixture was stirred for 75 minutes, during which a fine solid formed. The reaction mixture was filtered thru GF/F and the cake was washed with MeOH (20 mL). The filtrate was concentrated to about 15 mL under vacuum, isopropyl acetate (20 mL) was added, and the mixture was concentrated. To the concentrate was added isopropyl acetate (20 mL) and the mixture was stirred for 5 minutes. The phases were separated, and the organic layer was washed with 10% brine (20 mL). Citric acid (0.1 M, 20 mL) was added and the phases were vigorously mixed. The organic layer was removed and the aqueous was washed with isopropyl acetate (20 mL) and EtOAc (20 mL). To the aqueous layer was added isopropyl acetate (20 mL) and 50% NaOH (1 mL) was added. The phases were vigorously mixed and the aqueous was removed. The organic was washed with 10% brine (20 mL), dried over $Na_2SO_4$ and concentrated to 850 mg (85%).

Example 8

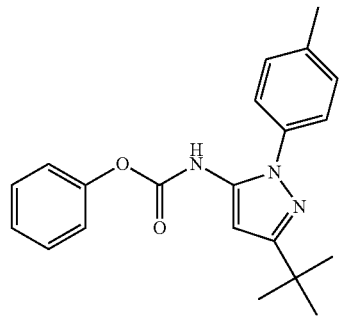

Phenyl 3-tert-butyl-1-p-tolyl-1H-pyrazol-1-5-ylcarbamate

To a solution of 3-tert-butyl-1-p-tolyl-1H-pyrazol-5-amine (102.9 g, 448.9 mmol) in EtOAc (1 L) at 10.9° C. was added a NaOH solution (2.5 M, 269 mL), and the biphasic reaction mixture warmed to 15.9 and then stabilized. Phenyl chloroformate (98.4 g, 156.5 mmol) was added in one portion and the temperature rose to 25.5 and then stabilized. The ice bath was removed and the reaction was monitored by HPLC. After 1 hour an additional 25 mL of 2.5 M NaOH was added. The reaction mixture was stirred overnight, and then diluted with EtOAc (200 mL). The organic layer was washed with brine (1 L), dried over $Na_2SO_4$ (200 g) and concentrated to about 400 to 500 mL of EtOAc. The concentrated solution was warmed to 60° C. After the solids had dissolved, heptane (2 L) was slowly added, during which solids formed. After stirring for 30 minutes the solid was collected via filtration and the cake was washed with 400-500 mL of heptane. The cake was dried in a vacuum oven at ambient temperature to yield 156.9 g (95.0%) of the title compound. $^1$H NMR (400 MHz, $CDCl_3$) δ 7.39-7.31 (m, 6H), 7.26-7.225 (m, 2H), 7.13 (br s, 2H), 6.96 (br s, 1H), 6.47 (br s, 1H), 2.42 (s, 3H), 1.34 (s, 9H).

Example 9

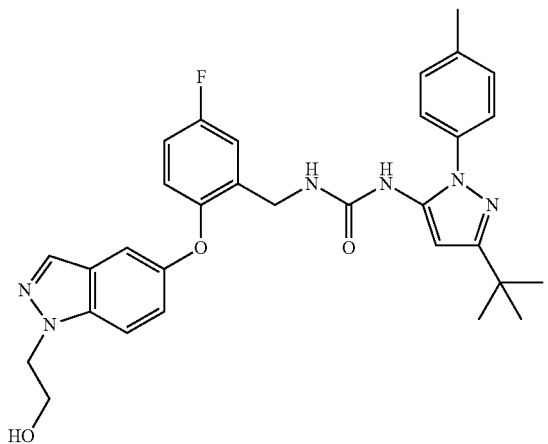

1-(3-tert-butyl-1-p-tolyl-1H-pyrazol-5-yl)-3-(5-fluoro-2-(1-(2-hydroxyethyl)-1H-indazol-5-yloxy)benzyl)urea (72)

To a 4.1° C. solution of 2-(5-(2-(aminomethyl)-4-fluorophenoxy)-1H-indazol-1-yl)ethanol (71.55 g, 237 mmol) in DMA (350 mL) was added a DMA (350 mL) solution of phenyl 3-tert-butyl-1-p-tolyl-1H-pyrazol-5-ylcarbamate (80.5 g, 230 mmol). The temperature rose to 18.4° C. and stabilized. The ice bath was removed and the reaction was stirred for 2 hours. An additional portion of 2-(5-(2-(aminomethyl)-4-fluorophenoxy)-1H-indazol-1-yl)ethanol was added and the reaction was stirred for 2 hours. The reaction mixture was partitioned between isopropyl acetate (1.6 L) and water (2.4 L). The aqueous layer was removed and the organic layer was washed with 0.5 N NaOH (2×2.4 L) and then saturated brine (1×2.4 L). The organic layer was dried over $Na_2SO_4$ (300 g) and concentrated to yield 110.8 g (86.6%).

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound of formula II

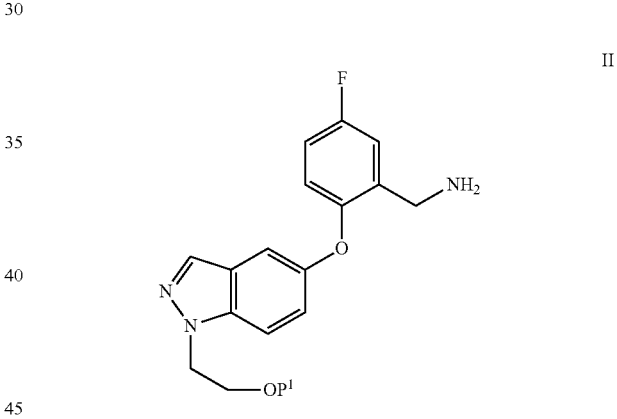

or a salt thereof, in which $P^1$ represents a hydrogen atom or a hydroxyl protecting group.

* * * * *